(12) United States Patent
Tsutsumi et al.

(10) Patent No.: US 7,271,139 B2
(45) Date of Patent: Sep. 18, 2007

(54) LIPOLYTIC ENZYME GENES

(75) Inventors: Noriko Tsutsumi, Ichikawa (JP); Jesper Vind, Vaerlose (DK); Shamkant Anant Patkar, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 11/474,151

(22) Filed: Jun. 23, 2006

(65) Prior Publication Data
US 2007/0010418 A1 Jan. 11, 2007

Related U.S. Application Data

(63) Continuation of application No. 10/250,824, filed as application No. PCT/DK02/00124 on Feb. 25, 2002.

(60) Provisional application No. 60/271,385, filed on Feb. 26, 2001.

(30) Foreign Application Priority Data

Feb. 23, 2001 (DK) .......................... PA 2001 0304

(51) Int. Cl.
*A21D 2/00* (2006.01)
*C12N 9/20* (2006.01)

(52) U.S. Cl. .................. 510/226; 426/20; 435/198; 536/23.2

(58) Field of Classification Search .................. 426/20; 510/226; 435/198; 536/23.2
See application file for complete search history.

(56) References Cited

U.S. PATENT DOCUMENTS

| | | | |
|---|---|---|---|
| 4,275,011 A | 6/1981 | Tanaka et al. | |
| 5,869,438 A | 2/1999 | Svendsen et al. | |
| 5,976,855 A | 11/1999 | Svendsen et al. | |
| 6,140,094 A | 10/2000 | Loffler et al. | |
| 6,159,687 A | 12/2000 | Vind | |

FOREIGN PATENT DOCUMENTS

| | | |
|---|---|---|
| EP | 0258 068 | 3/1988 |
| EP | 0575 133 A3 | 12/1993 |
| WO | WO92/19726 | 11/1992 |
| WO | WO95/22615 | 8/1995 |
| WO | WO97/04079 | 2/1997 |
| WO | WO97/07205 | 2/1997 |
| WO | WO97/07206 | 2/1997 |
| WO | WO98/31790 | 7/1998 |
| WO | WO 98/41622 | 9/1998 |
| WO | WO98/41622 | 9/1998 |
| WO | WO98/45453 | 10/1998 |
| WO | WO 00/32758 | 6/2000 |

OTHER PUBLICATIONS

Sequence search alignment between Applicants' SEQ ID No. 6 and Accession No. AAR22639 in WO92/05249.*

Sequence search alignment between Applicants' SEQ ID No. 6 and mature lipase (AAO19510) from Thermomyces ibadanensis in WO200262973-A2.*

Accension # AAR81990, Lipase of Humicola Lanuginosa, from WO9522615 (Aug, 24, 1995).

Accension # AR083396, Sequence 1 from Patent US 5976855, Method of preparing a variant of a lipolytic enzyme, (Nov. 2, 1999).

Accension # AAE05236, Sequence 2 from US5869438, Lipase Variants (Feb. 9, 1999).

Adekunle et al; Lipase Activity of Fourteen Fungi on Cucmeropsis, Nigerian Journal of Botany, vol. 9-10, pp. 35-40, (1996-1997).

Accension # AF054513, Thermomyces Lanuginosus, Submitted (Mar. 19, 1998) to the EMBL/GenBank/DDBJ databases.

Accension # A90761, Sequence 1 from WO 9831790, Protein with Phospholipase Activity, (Jul. 23, 1998).

Accension # EL6314; Gene Coding for Phospholipase A1 Derived from Aspergillus; Patent # JP1998155493-A1, (Jun. 16, 1998).

Accension # A84589; Sequence 8 from Patent WO 9845453, Lipase and use of Same for Improving Doughs and Baked Products, (Oct. 15, 1998).

Accension # A93428; Sequence 1 from Patent EP0808903; Recombinantly produced lysophospholipase from aspergillus, (Nov. 26, 1997).

B.A. Oso; The Lipase Activity of Talaromyces Emersonii.

Ogundero et al; Lipase Activities of Thermophilic Fungi from Mouldy Groundnuts in Nigeria, Mycologia, vol. 72, part 1, pp. 118-126 (1980).

Lattmann et al, Screening and Application of Microbial Esterases, Biocataysis, vol. 3, pp. 137-144 (1990).

Accension # 1998-391046, C1998-118412, From JP 10155493 (Abstract).

Crameri et al, DNA Shuffling of a family of genes from Diverse, Nature, vol. 391, pp. 288-291, (1998).

Kim et al; Substitution of Glycine 275 by Glutamate (G275E), J. Microbial Biotechnology, vol. 10, part 5, pp. 764-769 (2000).

Accension # A32008; Expression Cassette with Humicola Lanuginosa Lipase from Patent WO 9219726, (Nov. 12, 1992).

* cited by examiner

*Primary Examiner*—Tekchand Saidha
(74) *Attorney, Agent, or Firm*—Jason I. Garbell

(57) ABSTRACT

The inventors have isolated novel lipolytic enzyme genes with a high homology to the *T. lanuginosus* lipase gene and thus well suited for use in gene shuffling. Accordingly, the invention provides a method of generating genetic diversity into lipolytic enzymes by family shuffling of two or more homologous genes which encode lipolytic enzymes. The DNA shuffling technique is used to create a library of shuffled genes, and this is expressed in a suitable expression system and the expressed proteins are screened for lipolytic enzyme activity. The invention also provides a polynucleotide comprising a nucleotide sequence encoding a lipolytic enzyme and a lipolytic enzyme (a polypeptide with lipolytic enzyme activity).

7 Claims, 1 Drawing Sheet

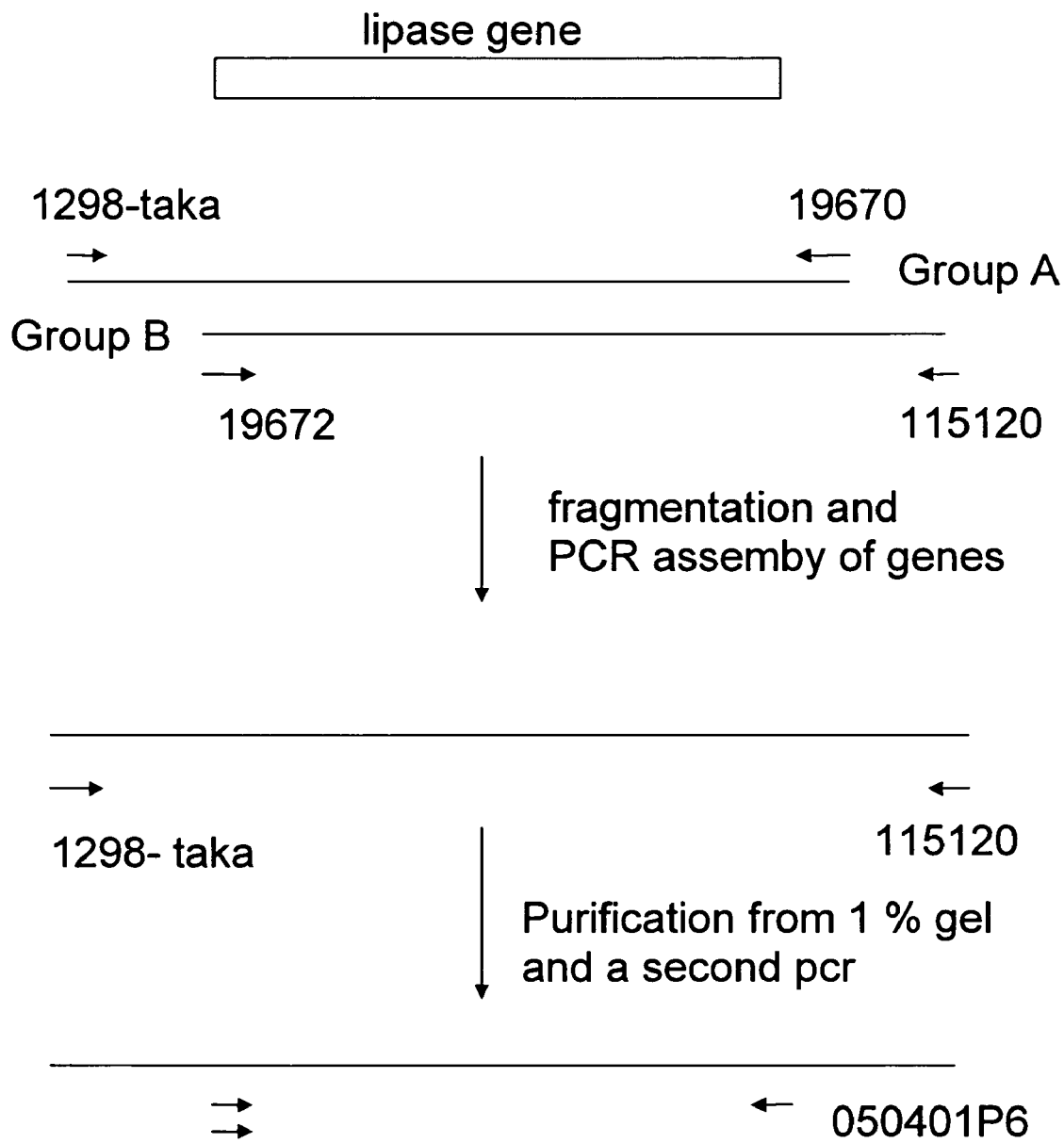

SEQUENCE LISTING

<160> NUMBER OF SEQ ID NOS: 53

<210> SEQ ID NO 1
<211> LENGTH: 918
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(66)
<220> FEATURE:
<221> NAME/KEY: mat_peptide
<222> LOCATION: (67)..()

<400> SEQUENCE: 1

```
atg agg agc tcc ctt gtg ctg ttc ttt gtc tct gcg tgg acg gcc ttg     48
Met Arg Ser Ser Leu Val Leu Phe Phe Val Ser Ala Trp Thr Ala Leu
        -20             -15                 -10 gcc agt cct att cgt cga gag gtc tcg cag gat ctg ttt aac cag ttc     96
Ala Ser Pro Ile Arg Arg Glu Val Ser Gln Asp Leu Phe Asn Gln Phe
     -5              -1  1                   5                  10 aat ctc ttt gca cag tat tct gca gcc gca tac tgc gga aaa aac aat    144
Asn Leu Phe Ala Gln Tyr Ser Ala Ala Ala Tyr Cys Gly Lys Asn Asn
                15                  20                  25
```

```
gat gcc cca gct ggt aca aac att acg tgc acg gga aat gcc tgc ccc      192
Asp Ala Pro Ala Gly Thr Asn Ile Thr Cys Thr Gly Asn Ala Cys Pro
             30                  35                  40 gag gta gag aag gcg gat gca acg ttt ctc tac tcg ttt gaa gac tct      240
Glu Val Glu Lys Ala Asp Ala Thr Phe Leu Tyr Ser Phe Glu Asp Ser
         45                  50                  55 gga gtg ggc gat gtc acc ggc ttc ctt gct ctc gac aac acg aac aaa      288
Gly Val Gly Asp Val Thr Gly Phe Leu Ala Leu Asp Asn Thr Asn Lys
     60                  65                  70 ttg atc gtc ctc tct ttc cgt ggc tct cgt tcc ata gag aac tgg atc      336
Leu Ile Val Leu Ser Phe Arg Gly Ser Arg Ser Ile Glu Asn Trp Ile
 75                  80                  85                  90 ggg aat ctt aac ttc gac ttg aaa gaa ata aat gac att tgc tcc ggc      384
Gly Asn Leu Asn Phe Asp Leu Lys Glu Ile Asn Asp Ile Cys Ser Gly
                 95                 100                 105 tgc agg gga cat gac ggc ttc act tcg tcc tgg agg tct gta gcc gat      432
Cys Arg Gly His Asp Gly Phe Thr Ser Ser Trp Arg Ser Val Ala Asp
            110                 115                 120 acg tta agg cag aag gtg gag gat gct gtg agg gag cat ccc gac tat      480
Thr Leu Arg Gln Lys Val Glu Asp Ala Val Arg Glu His Pro Asp Tyr
        125                 130                 135 cgc gtg gtg ttt acc gga cat agc ttg ggt ggt gca ttg gca act gtt      528
Arg Val Val Phe Thr Gly His Ser Leu Gly Gly Ala Leu Ala Thr Val
    140                 145                 150 gcc gga gca gac ctg cgt gga aat ggg tat gat atc gac gtg ttt tca      576
Ala Gly Ala Asp Leu Arg Gly Asn Gly Tyr Asp Ile Asp Val Phe Ser
155                 160                 165                 170 tat ggc gcc ccc cga gtc gga aac agg gct ttt gca gaa ttc ctg acc      624
Tyr Gly Ala Pro Arg Val Gly Asn Arg Ala Phe Ala Glu Phe Leu Thr
                175                 180                 185 gta cag acc ggc gga aca ctc tac cgc att acc cac acc aat gat att      672
Val Gln Thr Gly Gly Thr Leu Tyr Arg Ile Thr His Thr Asn Asp Ile
            190                 195                 200 gtc cct aga ctc ccg ccg cgc gaa ttc ggt tac agc cat tct agc cca      720
Val Pro Arg Leu Pro Pro Arg Glu Phe Gly Tyr Ser His Ser Ser Pro
        205                 210                 215 gag tac tgg atc aaa tct gga acc ctt gtc ccc gtc acc cga aac gat      768
Glu Tyr Trp Ile Lys Ser Gly Thr Leu Val Pro Val Thr Arg Asn Asp
    220                 225                 230 atc gtg aag ata gaa ggc atc gat gcc acc ggc ggt aat aac cag cct      816
Ile Val Lys Ile Glu Gly Ile Asp Ala Thr Gly Gly Asn Asn Gln Pro
235                 240                 245                 250 aac att ccg gat atc cct gcg cac cta tgg tac ttc ggg tta att ggg      864
Asn Ile Pro Asp Ile Pro Ala His Leu Trp Tyr Phe Gly Leu Ile Gly
                255                 260                 265 aca tgt ctt tagtggccgg cgcggctggg tccgactcta gcgagctcga gatct        918
Thr Cys Leu <210> SEQ ID NO 2
<211> LENGTH: 291
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
            -20                 -15                 -10

Ala Ser Pro Ile Arg Arg Glu Val Ser Gln Asp Leu Phe Asn Gln Phe
         -5              -1   1                   5                  10

Asn Leu Phe Ala Gln Tyr Ser Ala Ala Ala Tyr Cys Gly Lys Asn Asn
```

```
                          15                  20                  25
Asp Ala Pro Ala Thr Asn Ile Thr Cys Thr Gly Asn Ala Cys Pro
                30                  35                  40

Glu Val Glu Lys Ala Asp Ala Thr Phe Leu Tyr Ser Phe Glu Asp Ser
                45                  50                  55

Gly Val Gly Asp Val Thr Gly Phe Leu Ala Leu Asp Asn Thr Asn Lys
            60                  65                  70

Leu Ile Val Leu Ser Phe Arg Gly Ser Arg Ser Ile Glu Asn Trp Ile
75                  80                  85                  90

Gly Asn Leu Asn Phe Asp Leu Lys Glu Ile Asn Asp Ile Cys Ser Gly
                95                  100                 105

Cys Arg Gly His Asp Gly Phe Thr Ser Ser Trp Arg Ser Val Ala Asp
                110                 115                 120

Thr Leu Arg Gln Lys Val Glu Asp Ala Val Arg Glu His Pro Asp Tyr
                125                 130                 135

Arg Val Val Phe Thr Gly His Ser Leu Gly Gly Ala Leu Ala Thr Val
                140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
                190                 195                 200

Val Pro Arg Leu Pro Pro Arg Glu Phe Gly Tyr Ser His Ser Ser Pro
                205                 210                 215

Glu Tyr Trp Ile Lys Ser Gly Thr Leu Val Pro Val Thr Arg Asn Asp
            220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265

Thr Cys Leu

<210> SEQ ID NO 3
<211> LENGTH: 1083
<212> TYPE: DNA
<213> ORGANISM: Talaromyces thermophilus
<220> FEATURE:
<221> NAME/KEY: CDS
<222> LOCATION: (1)..(67)
<220> FEATURE:
<221> NAME/KEY: mat_peptide
<222> LOCATION: (67)..()
<220> FEATURE:
<221> NAME/KEY: CDS
<222> LOCATION: (139)..(307)
<220> FEATURE:
<221> NAME/KEY: CDS
<222> LOCATION: (370)..(703)
<220> FEATURE:
<221> NAME/KEY: CDS
<222> LOCATION: (778)..(1080)

<400> SEQUENCE: 3 atg agg agc tcg ctc gtg ctg ttc ttc gtt tct gcg tgg acg gcc ttg     48
Met Arg Ser Ser Leu Val Leu Phe Phe Val Ser Ala Trp Thr Ala Leu
        -20                 -15                 -10 gcc agt cct gtc cga cga g gtatgtaaat cacggggtat acttttcatg          97
Ala Ser Pro Val Arg Arg
    -5                  -1
```

```
cattgcatgt cgaacctgct gtactaagat tgcgcgcaca g ag  gtc tcg cag gat       152
                                              Glu Val Ser Gln Asp
                                                              5 ctg ttt gac cag ttc aac ctc ttt gcg cag tac tcg gcg gcc gca tac       200
Leu Phe Asp Gln Phe Asn Leu Phe Ala Gln Tyr Ser Ala Ala Ala Tyr
             10                  15                  20 tgc gcg aag aac aac gat gcc ccg gca ggt ggg aac gta acg tgc agg       248
Cys Ala Lys Asn Asn Asp Ala Pro Ala Gly Gly Asn Val Thr Cys Arg
         25                  30                  35 gga agt att tgc ccc gag gta gag aag gcg gat gca acg ttt ctc tac       296
Gly Ser Ile Cys Pro Glu Val Glu Lys Ala Asp Ala Thr Phe Leu Tyr
             40                  45                  50 tcg ttt gag ga  gtaggtgtca acaagagtac aggcacccgt agtagaaata           347
Ser Phe Glu Asp
         55 gcagactaac tgggaaatgt ag t tct gga gtt ggc gat gtc acc ggg ttc        397
                          Ser Gly Val Gly Asp Val Thr Gly Phe
                                      60                  65 ctt gct ctc gac aac acg aac aga ctg atc gtc ctc tct ttc cgc ggc       445
Leu Ala Leu Asp Asn Thr Asn Arg Leu Ile Val Leu Ser Phe Arg Gly
             70                  75                  80 tct cgt tcc ctg gaa aac tgg atc ggg aat atc aac ttg gac ttg aaa       493
Ser Arg Ser Leu Glu Asn Trp Ile Gly Asn Ile Asn Leu Asp Leu Lys
             85                  90                  95 gga att gac gac atc tgc tct ggc tgc aag gga cat gac ggc ttc act       541
Gly Ile Asp Asp Ile Cys Ser Gly Cys Lys Gly His Asp Gly Phe Thr
        100                 105                 110 tcc tcc tgg agg tcc gtt gcc aat acc ttg act cag caa gtg cag aat       589
Ser Ser Trp Arg Ser Val Ala Asn Thr Leu Thr Gln Gln Val Gln Asn
115                 120                 125                 130 gct gtg agg gag cat ccc gac tac cgc gtc gtc ttc act ggg cac agc       637
Ala Val Arg Glu His Pro Asp Tyr Arg Val Val Phe Thr Gly His Ser
                135                 140                 145 ttg ggt ggt gca ttg gca act gtg gcc ggg gca tct ctg cgt gga aat       685
Leu Gly Gly Ala Leu Ala Thr Val Ala Gly Ala Ser Leu Arg Gly Asn
            150                 155                 160 ggg tac gat ata gat gtg gtatgtagga aaaatgatcc ccgtggagcg              733
Gly Tyr Asp Ile Asp Val
            165 gtcatgtgga aatgtgcagg ggtgtctaat acacagacca acag ttc tca tat ggc      789
                                                 Phe Ser Tyr Gly
                                                         170 gct ccc cgc gtc gga aac agg gct ttt gcg gaa ttc ctg acc gca cag       837
Ala Pro Arg Val Gly Asn Arg Ala Phe Ala Glu Phe Leu Thr Ala Gln
        175                 180                 185 acc ggc ggc acc ttg tac cgc atc acc cac acc aat gat att gtc ccc       885
Thr Gly Gly Thr Leu Tyr Arg Ile Thr His Thr Asn Asp Ile Val Pro
        190                 195                 200 aga ctc ccg cca cgc gaa ttg ggt tac agc cat tct agc cca gag tat       933
Arg Leu Pro Pro Arg Glu Leu Gly Tyr Ser His Ser Ser Pro Glu Tyr
205                 210                 215                 220 tgg atc acg tct gga acc ctc gtc cca gtg acc aag aac gat atc gtc       981
Trp Ile Thr Ser Gly Thr Leu Val Pro Val Thr Lys Asn Asp Ile Val
                225                 230                 235 aag gtg gag ggc atc gat tcc acc gat gga aac aac cag cca aat acc      1029
Lys Val Glu Gly Ile Asp Ser Thr Asp Gly Asn Asn Gln Pro Asn Thr
            240                 245                 250 ccg gac att gct gcg cac cta tgg tac ttc ggg tca atg gcg acg tgt      1077
Pro Asp Ile Ala Ala His Leu Trp Tyr Phe Gly Ser Met Ala Thr Cys
```

```
                    255                 260                 265
ttg taa                                                                        1083
Leu <210> SEQ ID NO 4
<211> LENGTH: 291
<212> TYPE: PRT
<213> ORGANISM: Talaromyces thermophilus

<400> SEQUENCE: 4

Met Arg Ser Ser Leu Val Leu Phe Phe Val Ser Ala Trp Thr Ala Leu
        -20                 -15                 -10

Ala Ser Pro Val Arg Arg Glu Val Ser Gln Asp Leu Phe Asp Gln Phe
    -5              -1  1               5                   10

Asn Leu Phe Ala Gln Tyr Ser Ala Ala Tyr Cys Ala Lys Asn Asn
                15                  20                  25

Asp Ala Pro Ala Gly Gly Asn Val Thr Cys Arg Gly Ser Ile Cys Pro
            30                  35                  40

Glu Val Glu Lys Ala Asp Ala Thr Phe Leu Tyr Ser Phe Glu Asp Ser
        45                  50                  55

Gly Val Gly Asp Val Thr Gly Phe Leu Ala Leu Asp Asn Thr Asn Arg
    60                  65                  70

Leu Ile Val Leu Ser Phe Arg Gly Ser Arg Ser Leu Glu Asn Trp Ile
75                  80                  85                  90

Gly Asn Ile Asn Leu Asp Leu Lys Gly Ile Asp Asp Ile Cys Ser Gly
                95                  100                 105

Cys Lys Gly His Asp Gly Phe Thr Ser Ser Trp Arg Ser Val Ala Asn
            110                 115                 120

Thr Leu Thr Gln Gln Val Gln Asn Ala Val Arg Glu His Pro Asp Tyr
        125                 130                 135

Arg Val Val Phe Thr Gly His Ser Leu Gly Gly Ala Leu Ala Thr Val
    140                 145                 150

Ala Gly Ala Ser Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Ala Gln Thr Gly Gly Thr Leu Tyr Arg Ile Thr His Thr Asn Asp Ile
            190                 195                 200

Val Pro Arg Leu Pro Pro Arg Glu Leu Gly Tyr Ser His Ser Ser Pro
        205                 210                 215

Glu Tyr Trp Ile Thr Ser Gly Thr Leu Val Pro Val Thr Lys Asn Asp
    220                 225                 230

Ile Val Lys Val Glu Gly Ile Asp Ser Thr Asp Gly Asn Asn Gln Pro
235                 240                 245                 250

Asn Thr Pro Asp Ile Ala Ala His Leu Trp Tyr Phe Gly Ser Met Ala
                255                 260                 265

Thr Cys Leu

<210> SEQ ID NO 5
<211> LENGTH: 1070
<212> TYPE: DNA
<213> ORGANISM: Thermomyces ibadanensis
<220> FEATURE:
<221> NAME/KEY: CDS
<222> LOCATION: (1)..(67)
<220> FEATURE:
<221> NAME/KEY: mat_peptide
```

```
<222> LOCATION: (67)..()
<220> FEATURE:
<221> NAME/KEY: CDS
<222> LOCATION: (128)..(296)
<220> FEATURE:
<221> NAME/KEY: CDS
<222> LOCATION: (357)..(690)
<220> FEATURE:
<221> NAME/KEY: CDS
<222> LOCATION: (765)..(1067)

<400> SEQUENCE: 5 atg cgg agc tcc ctc gtg ctg ttc ttc ctc tct gcg tgg acg gcc ttg       48
Met Arg Ser Ser Leu Val Leu Phe Phe Leu Ser Ala Trp Thr Ala Leu
        -20              -15                  -10 gcg cgg cct gtt cga cga g gtatgtagca aggacactta ttacatgttg            97
Ala Arg Pro Val Arg Arg
        -5          -1 accttggtga ttctaagact gcatgcgcag cg  gtt ccg caa gat ctg ctc gac     150
                                    Ala Val Pro Gln Asp Leu Leu Asp
                                                            5 cag ttt gaa ctc ttt tca caa tat tcg gcg gcc gca tac tgt gcg gca      198
Gln Phe Glu Leu Phe Ser Gln Tyr Ser Ala Ala Ala Tyr Cys Ala Ala
        10                  15                  20 aac aat cat gct cca gtg ggc tca gac gta acg tgc tcg gag aat gtc      246
Asn Asn His Ala Pro Val Gly Ser Asp Val Thr Cys Ser Glu Asn Val
25                  30                  35                  40 tgc cct gag gta gat gcg gcg gac gca acg ttt ctc tat tct ttt gaa      294
Cys Pro Glu Val Asp Ala Ala Asp Ala Thr Phe Leu Tyr Ser Phe Glu
                    45                  50                  55 ga gtgggtgtcg acaaagcaca gagacagtag tagagacagc agtctaactg             346
Asp agatgtgcag t tct gga tta ggc gat gtt acc ggc ctt ctc gct ctc gac     396
             Ser Gly Leu Gly Asp Val Thr Gly Leu Leu Ala Leu Asp
                         60                  65                  70 aac acg aat aaa ctg atc gtc ctc tct ttc cgc ggc tct cgc tca gta      444
Asn Thr Asn Lys Leu Ile Val Leu Ser Phe Arg Gly Ser Arg Ser Val
                75                  80                  85 gag aac tgg atc gcg aac ctc gcc gcc gac ctg aca gaa ata tct gac      492
Glu Asn Trp Ile Ala Asn Leu Ala Ala Asp Leu Thr Glu Ile Ser Asp
        90                  95                  100 atc tgc tcc ggc tgc gag ggg cat gtc ggc ttc gtt act tct tgg agg      540
Ile Cys Ser Gly Cys Glu Gly His Val Gly Phe Val Thr Ser Trp Arg
        105                 110                 115 tct gta gcc gac act ata agg gag cag gtg cag aat gcc gtg aac gag      588
Ser Val Ala Asp Thr Ile Arg Glu Gln Val Gln Asn Ala Val Asn Glu
        120                 125                 130 cat ccc gat tac cgc gtg gtc ttt acc gga cat agc ttg gga ggc gca      636
His Pro Asp Tyr Arg Val Val Phe Thr Gly His Ser Leu Gly Gly Ala
135                 140                 145                 150 ctg gca act att gcc gca gca gct ctg cga gga aat gga tac aat atc      684
Leu Ala Thr Ile Ala Ala Ala Ala Leu Arg Gly Asn Gly Tyr Asn Ile
                155                 160                 165 gac gtg gtatgtggga agaagccacc cagacaaaca attatgtgga aacatgcaag       740
Asp Val gatggctaat acacggtcca acag ttc tca tat ggc gcg ccc cgc gtc ggt       791
                         Phe Ser Tyr Gly Ala Pro Arg Val Gly
                                     170                 175 aac agg gca ttt gca gaa ttc ctg acc gca cag acg ggc ggc acc ctg      839
Asn Arg Ala Phe Ala Glu Phe Leu Thr Ala Gln Thr Gly Gly Thr Leu
        180                 185                 190
```

-continued

```
tat cgc atc acc cat acc aat gat atc gtc cct aga ctc cct cct cga    887
Tyr Arg Ile Thr His Thr Asn Asp Ile Val Pro Arg Leu Pro Pro Arg
    195                 200                 205 gac tgg ggt tac agc cac tct agc ccg gag tac tgg gtc acg tct ggt    935
Asp Trp Gly Tyr Ser His Ser Ser Pro Glu Tyr Trp Val Thr Ser Gly
210                 215                 220                 225 aac gac gtc cca gtg acc gca aac gac atc acc gtc gtg gag ggc atc    983
Asn Asp Val Pro Val Thr Ala Asn Asp Ile Thr Val Val Glu Gly Ile
                230                 235                 240 gat tcc acc gac ggg aac aac cag ggg aat atc cca gac atc cct tcg    1031
Asp Ser Thr Asp Gly Asn Asn Gln Gly Asn Ile Pro Asp Ile Pro Ser
        245                 250                 255 cat cta tgg tat ttc ggt ccc att tca gag tgt gat tag                1070
His Leu Trp Tyr Phe Gly Pro Ile Ser Glu Cys Asp
        260                 265
```

<210> SEQ ID NO 6
<211> LENGTH: 291
<212> TYPE: PRT
<213> ORGANISM: Thermomyces ibadanensis

<400> SEQUENCE: 6

```
Met Arg Ser Ser Leu Val Leu Phe Phe Leu Ser Ala Trp Thr Ala Leu
    -20                 -15                 -10

Ala Arg Pro Val Arg Arg Ala Val Pro Gln Asp Leu Leu Asp Gln Phe
 -5              -1  1               5                       10

Glu Leu Phe Ser Gln Tyr Ser Ala Ala Tyr Cys Ala Ala Asn Asn
                15                  20                  25

His Ala Pro Val Gly Ser Asp Val Thr Cys Ser Glu Asn Val Cys Pro
                30                  35                  40

Glu Val Asp Ala Ala Asp Ala Thr Phe Leu Tyr Ser Phe Glu Asp Ser
                45                  50                  55

Gly Leu Gly Asp Val Thr Gly Leu Leu Ala Leu Asp Asn Thr Asn Lys
 60                  65                  70

Leu Ile Val Leu Ser Phe Arg Gly Ser Arg Ser Val Glu Asn Trp Ile
 75                  80                  85                  90

Ala Asn Leu Ala Ala Asp Leu Thr Glu Ile Ser Asp Ile Cys Ser Gly
                 95                 100                 105

Cys Glu Gly His Val Gly Phe Val Thr Ser Trp Arg Ser Val Ala Asp
                110                 115                 120

Thr Ile Arg Glu Gln Val Gln Asn Ala Val Asn Glu His Pro Asp Tyr
                125                 130                 135

Arg Val Val Phe Thr Gly His Ser Leu Gly Gly Ala Leu Ala Thr Ile
    140                 145                 150

Ala Ala Ala Ala Leu Arg Gly Asn Gly Tyr Asn Ile Asp Val Phe Ser
155                 160                 165                 170

Tyr Gly Ala Pro Arg Val Gly Asn Arg Ala Phe Ala Glu Phe Leu Thr
                175                 180                 185

Ala Gln Thr Gly Gly Thr Leu Tyr Arg Ile Thr His Thr Asn Asp Ile
            190                 195                 200

Val Pro Arg Leu Pro Pro Arg Asp Trp Gly Tyr Ser His Ser Ser Pro
    205                 210                 215

Glu Tyr Trp Val Thr Ser Gly Asn Asp Val Pro Val Thr Ala Asn Asp
    220                 225                 230

Ile Thr Val Val Glu Gly Ile Asp Ser Thr Asp Gly Asn Asn Gln Gly
235                 240                 245                 250
```

```
Asn Ile Pro Asp Ile Pro Ser His Leu Trp Tyr Phe Gly Pro Ile Ser
            255                 260                 265

Glu Cys Asp

<210> SEQ ID NO 7
<211> LENGTH: 1064
<212> TYPE: DNA
<213> ORGANISM: Talaromyces emersonii
<220> FEATURE:
<221> NAME/KEY: CDS
<222> LOCATION: (1)..(88)
<220> FEATURE:
<221> NAME/KEY: mat_peptide
<222> LOCATION: (88)..()
<220> FEATURE:
<221> NAME/KEY: CDS
<222> LOCATION: (142)..(310)
<220> FEATURE:
<221> NAME/KEY: CDS
<222> LOCATION: (362)..(695)
<220> FEATURE:
<221> NAME/KEY: CDS
<222> LOCATION: (756)..(1061)

<400> SEQUENCE: 7 atg ttc aaa tcg gcc gct gtg cgg gcc att gct gcc ctc gga ctg act         48
Met Phe Lys Ser Ala Ala Val Arg Ala Ile Ala Ala Leu Gly Leu Thr
            -25                 -20                 -15 gcg tca gtc ttg gct gct cct gtt gaa ctg ggc cgt cga g gtaaggaagc        98
Ala Ser Val Leu Ala Ala Pro Val Glu Leu Gly Arg Arg
        -10                 -5                  -1 atgacggaga gaacaccctg tgcgacctgc tgacatcctt cag at gtt tct cag         152
                                                Asp Val Ser Gln gac ctc ttc gac cag ctc aat ctt ttc gag cag tac tcg gcg gct gcg        200
Asp Leu Phe Asp Gln Leu Asn Leu Phe Glu Gln Tyr Ser Ala Ala Ala
5                   10                  15                  20 tac tgt tca gct aac aat gag gcc tct gcc ggc acg gca atc tct tgc        248
Tyr Cys Ser Ala Asn Asn Glu Ala Ser Ala Gly Thr Ala Ile Ser Cys
                25                  30                  35 tcc gca ggc aat tgc ccg ttg gtc cag cag gct gga gca acc atc ctg        296
Ser Ala Gly Asn Cys Pro Leu Val Gln Gln Ala Gly Ala Thr Ile Leu
            40                  45                  50 tat tca ttc aac aa gtgggtgtca cggaaaagat tgttgatacc aacatgttga        350
Tyr Ser Phe Asn Asn
            55 cgtgttgtca g c att ggc tct ggc gat gtg acg ggt ttt ctc gct ctc        398
              Ile Gly Ser Gly Asp Val Thr Gly Phe Leu Ala Leu
                      60                  65 gac tcg acg aat caa ttg atc gtc ttg tca ttc cgg gga tca gag act        446
Asp Ser Thr Asn Gln Leu Ile Val Leu Ser Phe Arg Gly Ser Glu Thr
70                  75                  80                  85 ctc gaa aac tgg atc gct gac ctg gaa gct gac ctg gtc gat gcc tct        494
Leu Glu Asn Trp Ile Ala Asp Leu Glu Ala Asp Leu Val Asp Ala Ser
                90                  95                  100 gcc atc tgt tcc ggc tgt gaa gca cac gat ggg ttc ctt tca tcc tgg        542
Ala Ile Cys Ser Gly Cys Glu Ala His Asp Gly Phe Leu Ser Ser Trp
            105                 110                 115 aat tca gtc gcc agc act ctg aca tcc aaa atc tcg tcg gcc gtc aac        590
Asn Ser Val Ala Ser Thr Leu Thr Ser Lys Ile Ser Ser Ala Val Asn
        120                 125                 130 gaa cat ccc agc tac aag ctg gtc ttc acc ggc cac agt ctc gga gcc        638
Glu His Pro Ser Tyr Lys Leu Val Phe Thr Gly His Ser Leu Gly Ala
    135                 140                 145
```

```
gcc ttg gct aca ctt gga gcc gtt tct ctt aga gag agc gga tat aat      686
Ala Leu Ala Thr Leu Gly Ala Val Ser Leu Arg Glu Ser Gly Tyr Asn
150             155                 160                 165 att gac ctc gtaagtttcc ggcacgggcg tcgtcatcat cgagcggaaa               735
Ile Asp Leu gactgaccgg ttaactgcag tac aat tat ggc tgc ccc cgg gtc ggt aac acc    788
                     Tyr Asn Tyr Gly Cys Pro Arg Val Gly Asn Thr
                                 170                 175 gcg ctc gca gac ttc atc acc acg caa tcc gga ggc aca aat tac cgc      836
Ala Leu Ala Asp Phe Ile Thr Thr Gln Ser Gly Gly Thr Asn Tyr Arg
180             185                 190                 195 gtc acg cat tcc gat gac cct gtc ccc aag ctg cct ccc agg agt ttt      884
Val Thr His Ser Asp Asp Pro Val Pro Lys Leu Pro Pro Arg Ser Phe
                200                 205                 210 gga tac agc caa ccg agc cca gag tac tgg atc acc tca ggg aac aat      932
Gly Tyr Ser Gln Pro Ser Pro Glu Tyr Trp Ile Thr Ser Gly Asn Asn
                215                 220                 225 gta act gtt caa ccg tcc gac atc gag gtc atc gaa ggc gtc gac tcc      980
Val Thr Val Gln Pro Ser Asp Ile Glu Val Ile Glu Gly Val Asp Ser
230             235                 240 act gca ggc aac gac ggc acc cct gct ggc ctt gac att gat gct cat     1028
Thr Ala Gly Asn Asp Gly Thr Pro Ala Gly Leu Asp Ile Asp Ala His
245             250                 255 cgg tgg tac ttt gga ccc att agc gca tgt tcg tga                     1064
Arg Trp Tyr Phe Gly Pro Ile Ser Ala Cys Ser
260             265                 270
```

<210> SEQ ID NO 8
<211> LENGTH: 299
<212> TYPE: PRT
<213> ORGANISM: Talaromyces emersonii

<400> SEQUENCE: 8

```
Met Phe Lys Ser Ala Ala Val Arg Ala Ile Ala Ala Leu Gly Leu Thr
                -25                 -20                 -15

Ala Ser Val Leu Ala Ala Pro Val Glu Leu Gly Arg Arg Asp Val Ser
            -10                  -5                  -1   1

Gln Asp Leu Phe Asp Gln Leu Asn Leu Phe Glu Gln Tyr Ser Ala Ala
 5                  10                  15

Ala Tyr Cys Ser Ala Asn Asn Glu Ala Ser Ala Gly Thr Ala Ile Ser
 20                 25                  30                  35

Cys Ser Ala Gly Asn Cys Pro Leu Val Gln Gln Ala Gly Ala Thr Ile
                40                  45                  50

Leu Tyr Ser Phe Asn Asn Ile Gly Ser Gly Asp Val Thr Gly Phe Leu
                55                  60                  65

Ala Leu Asp Ser Thr Asn Gln Leu Ile Val Leu Ser Phe Arg Gly Ser
            70                  75                  80

Glu Thr Leu Glu Asn Trp Ile Ala Asp Leu Glu Ala Asp Leu Val Asp
            85                  90                  95

Ala Ser Ala Ile Cys Ser Gly Cys Glu Ala His Asp Gly Phe Leu Ser
100                 105                 110                 115

Ser Trp Asn Ser Val Ala Ser Thr Leu Thr Ser Lys Ile Ser Ser Ala
                120                 125                 130

Val Asn Glu His Pro Ser Tyr Lys Val Phe Thr Gly His Ser Leu
                135                 140                 145

Gly Ala Ala Leu Ala Thr Leu Gly Ala Val Ser Leu Arg Glu Ser Gly
            150                 155                 160
```

```
Tyr Asn Ile Asp Leu Tyr Asn Tyr Gly Cys Pro Arg Val Gly Asn Thr
165                 170                 175

Ala Leu Ala Asp Phe Ile Thr Thr Gln Ser Gly Gly Thr Asn Tyr Arg
180                 185                 190                 195

Val Thr His Ser Asp Asp Pro Val Pro Lys Leu Pro Pro Arg Ser Phe
                200                 205                 210

Gly Tyr Ser Gln Pro Ser Pro Glu Tyr Trp Ile Thr Ser Gly Asn Asn
            215                 220                 225

Val Thr Val Gln Pro Ser Asp Ile Glu Val Ile Glu Gly Val Asp Ser
        230                 235                 240

Thr Ala Gly Asn Asp Gly Thr Pro Ala Gly Leu Asp Ile Asp Ala His
    245                 250                 255

Arg Trp Tyr Phe Gly Pro Ile Ser Ala Cys Ser
260                 265                 270

<210> SEQ ID NO 9
<211> LENGTH: 1074
<212> TYPE: DNA
<213> ORGANISM: Talaromyces byssochlamydoides
<220> FEATURE:
<221> NAME/KEY: CDS
<222> LOCATION: (1)..(85)
<220> FEATURE:
<221> NAME/KEY: mat_peptide
<222> LOCATION: (85)..()
<220> FEATURE:
<221> NAME/KEY: CDS
<222> LOCATION: (150)..(318)
<220> FEATURE:
<221> NAME/KEY: CDS
<222> LOCATION: (376)..(709)
<220> FEATURE:
<221> NAME/KEY: CDS
<222> LOCATION: (760)..(1071)

<400> SEQUENCE: 9 atg ttc aaa tca act gtc cgg gcc atc gcc gcc ctc gga ctg acc tcg      48
Met Phe Lys Ser Thr Val Arg Ala Ile Ala Ala Leu Gly Leu Thr Ser
                -25                 -20                 -15 tca gtc ttt gct gct cct atc gaa ctg ggc cgt cga g gtaaggggca         95
Ser Val Phe Ala Ala Pro Ile Glu Leu Gly Arg Arg
        -10                 -5                  -1 tgaaaactcc ctgtatggca tctcatctgg cagcatatct actgacatcc tcag at      151
                                                               Asp gtt tcg gag cag ctc ttc aac cag ttc aat ctc ttc gag cag tat tcc     199
Val Ser Glu Gln Leu Phe Asn Gln Phe Asn Leu Phe Glu Gln Tyr Ser
         5                  10                  15 gcg gct gcg tac tgt cca gcc aac ttt gag tcc gct tcc ggc gcg gca     247
Ala Ala Ala Tyr Cys Pro Ala Asn Phe Glu Ser Ala Ser Gly Ala Ala
                 20                  25                  30 att tct tgt tcc aca ggc aat tgc ccg ctc gtc caa cag gct ggc gca     295
Ile Ser Cys Ser Thr Gly Asn Cys Pro Leu Val Gln Gln Ala Gly Ala
         35                  40                  45 acc acc ctg tat gca ttc aac aa  gtgagtgtca tggaaaggct gttggtaca     348
Thr Thr Leu Tyr Ala Phe Asn Asn
 50                  55 ccgtacgggt atgttgactg tcatcag c atc ggc tct ggc gat gtg acg ggt     400
                               Ile Gly Ser Gly Asp Val Thr Gly
                                            60                  65 ttt ctt gct gtc gat ccg acc aac cga ctc atc gtc ttg tcg ttc cgg     448
Phe Leu Ala Val Asp Pro Thr Asn Arg Leu Ile Val Leu Ser Phe Arg
             70                  75                  80
```

-continued

```
ggg tca gag agt ctc gag aac tgg atc act aat ctc agc gcc gac ctg      496
Gly Ser Glu Ser Leu Glu Asn Trp Ile Thr Asn Leu Ser Ala Asp Leu
         85                  90                  95 gtc gat gcc tct gca atc tgt tcc ggg tgt gaa gcc cat gac gga ttc      544
Val Asp Ala Ser Ala Ile Cys Ser Gly Cys Glu Ala His Asp Gly Phe
    100                 105                 110 tat tcg tct tgg caa tca gtt gcc agc act ctg acc tcc caa atc tcg      592
Tyr Ser Ser Trp Gln Ser Val Ala Ser Thr Leu Thr Ser Gln Ile Ser
115                 120                 125 tcg gcc ctc tcg gca tat cca aac tac aag ctg gtc ttc acc ggc cac      640
Ser Ala Leu Ser Ala Tyr Pro Asn Tyr Lys Leu Val Phe Thr Gly His
130                 135                 140                 145 agt ctc gga gcc gcc tta gct aca ctt gga gct gtc tct ctc agg gag      688
Ser Leu Gly Ala Ala Leu Ala Thr Leu Gly Ala Val Ser Leu Arg Glu
                150                 155                 160 agt gga tac aat atc gac ctc gtaagttcct ggcattgcca tcatggaaag         739
Ser Gly Tyr Asn Ile Asp Leu
                165 agactcacag ttaactgtag tac aac ttt ggc tgt ccc cgg gtc ggc aac act    792
                      Tyr Asn Phe Gly Cys Pro Arg Val Gly Asn Thr
                                      170                 175 gcg ctc gca gac ttt att acc aac caa acc ggt ggc aca aat tac cgg      840
Ala Leu Ala Asp Phe Ile Thr Asn Gln Thr Gly Gly Thr Asn Tyr Arg
180                 185                 190                 195 gta acg cat tac gag gac cct gtc ccc aag ctg cct ccc agg agt ttt      888
Val Thr His Tyr Glu Asp Pro Val Pro Lys Leu Pro Pro Arg Ser Phe
                200                 205                 210 gga tac agc caa cct agc ccg gaa tac tgg atc acg tcg gga aac aat      936
Gly Tyr Ser Gln Pro Ser Pro Glu Tyr Trp Ile Thr Ser Gly Asn Asn
                215                 220                 225 gtg act gtg act tcg tcc gac atc gat gtc gtc gtg ggt gtc gac tcg      984
Val Thr Val Thr Ser Ser Asp Ile Asp Val Val Val Gly Val Asp Ser
                230                 235                 240 act gca ggc aac gac ggg acg cct gat ggc ctt gac act gct gcc cat     1032
Thr Ala Gly Asn Asp Gly Thr Pro Asp Gly Leu Asp Thr Ala Ala His
245                 250                 255 agg tgg tat ttt gga cct act acc gaa tgt tcg tcg tca tga             1074
Arg Trp Tyr Phe Gly Pro Thr Thr Glu Cys Ser Ser Ser
260                 265                 270
```

<210> SEQ ID NO 10
<211> LENGTH: 300
<212> TYPE: PRT
<213> ORGANISM: Talaromyces byssochlamydoides

<400> SEQUENCE: 10

```
Met Phe Lys Ser Thr Val Arg Ala Ile Ala Ala Leu Gly Leu Thr Ser
            -25                 -20                 -15

Ser Val Phe Ala Ala Pro Ile Glu Leu Gly Arg Arg Asp Val Ser Glu
        -10                 -5          -1  1

Gln Leu Phe Asn Gln Phe Asn Leu Phe Glu Gln Tyr Ser Ala Ala Ala
5                   10                  15                  20

Tyr Cys Pro Ala Asn Phe Glu Ser Ala Ser Gly Ala Ala Ile Ser Cys
                25                  30                  35

Ser Thr Gly Asn Cys Pro Leu Val Gln Gln Ala Gly Ala Thr Thr Leu
            40                  45                  50

Tyr Ala Phe Asn Asn Ile Gly Ser Gly Asp Val Thr Gly Phe Leu Ala
        55                  60                  65

Val Asp Pro Thr Asn Arg Leu Ile Val Leu Ser Phe Arg Gly Ser Glu
```

```
                    70                  75                  80
Ser Leu Glu Asn Trp Ile Thr Asn Leu Ser Ala Asp Leu Val Asp Ala
 85                  90                  95                 100

Ser Ala Ile Cys Ser Gly Cys Glu Ala His Asp Gly Phe Tyr Ser Ser
                105                 110                 115

Trp Gln Ser Val Ala Ser Thr Leu Thr Ser Gln Ile Ser Ser Ala Leu
                120                 125                 130

Ser Ala Tyr Pro Asn Tyr Lys Leu Val Phe Thr Gly His Ser Leu Gly
                135                 140                 145

Ala Ala Leu Ala Thr Leu Gly Ala Val Ser Leu Arg Glu Ser Gly Tyr
                150                 155                 160

Asn Ile Asp Leu Tyr Asn Phe Gly Cys Pro Arg Val Gly Asn Thr Ala
165                 170                 175                 180

Leu Ala Asp Phe Ile Thr Asn Gln Thr Gly Gly Thr Asn Tyr Arg Val
                185                 190                 195

Thr His Tyr Glu Asp Pro Val Pro Lys Leu Pro Arg Ser Phe Gly
                200                 205                 210

Tyr Ser Gln Pro Ser Pro Glu Tyr Trp Ile Thr Ser Gly Asn Asn Val
                215                 220                 225

Thr Val Thr Ser Ser Asp Ile Asp Val Val Gly Val Asp Ser Thr
230                 235                 240

Ala Gly Asn Asp Gly Thr Pro Asp Gly Leu Asp Thr Ala Ala His Arg
245                 250                 255                 260

Trp Tyr Phe Gly Pro Thr Thr Glu Cys Ser Ser Ser
                265                 270

<210> SEQ ID NO 11
<211> LENGTH: 51
<212> TYPE: DNA
<213> ORGANISM: Artificial Sequence
<220> FEATURE:
<221> NAME/KEY: misc_feature
<223> OTHER INFORMATION: 051200j1

<400> SEQUENCE: 11
ggggacaagt ttgtacaaaa aagcaggacc atgaggagct cgctcgtgct g            51

<210> SEQ ID NO 12
<211> LENGTH: 39
<212> TYPE: DNA
<213> ORGANISM: Artificial Sequence
<220> FEATURE:
<221> NAME/KEY: misc_feature
<223> OTHER INFORMATION: 051200J2

<400> SEQUENCE: 12
ccagtcctgt ccgacgagag gtctcgcagg atctgtttg                          39

<210> SEQ ID NO 13
<211> LENGTH: 39
<212> TYPE: DNA
<213> ORGANISM: Artificial Sequence
<220> FEATURE:
<221> NAME/KEY: misc_feature
<223> OTHER INFORMATION: 051200J3

<400> SEQUENCE: 13
caaacagatc ctgcgagacc tctcgtcgga caggactgg                          39

<210> SEQ ID NO 14
```

```
<211> LENGTH: 39
<212> TYPE: DNA
<213> ORGANISM: Artificial Sequence
<220> FEATURE:
<221> NAME/KEY: misc_feature
<223> OTHER INFORMATION: 051200J4

<400> SEQUENCE: 14
tctctactcg tttgaggatt ctggagttgg cgatgtcac                          39

<210> SEQ ID NO 15
<211> LENGTH: 36
<212> TYPE: DNA
<213> ORGANISM: Artificial Sequence
<220> FEATURE:
<221> NAME/KEY: misc_feature
<223> OTHER INFORMATION: 051200J5

<400> SEQUENCE: 15
acatcgccaa ctccagaatc ctcaaacgag tagaga                             36

<210> SEQ ID NO 16
<211> LENGTH: 36
<212> TYPE: DNA
<213> ORGANISM: Artificial Sequence
<220> FEATURE:
<221> NAME/KEY: misc_feature
<223> OTHER INFORMATION: 051200J6

<400> SEQUENCE: 16
gggtacgata tagatgtgtt ctcatatggc gctccc                             36

<210> SEQ ID NO 17
<211> LENGTH: 36
<212> TYPE: DNA
<213> ORGANISM: Artificial Sequence
<220> FEATURE:
<221> NAME/KEY: misc_feature
<223> OTHER INFORMATION: 051200J7

<400> SEQUENCE: 17
gggagcgcca tatgagaaca catctatatc gtaccc                             36

<210> SEQ ID NO 18
<211> LENGTH: 48
<212> TYPE: DNA
<213> ORGANISM: Artificial Sequence
<220> FEATURE:
<221> NAME/KEY: misc_feature
<223> OTHER INFORMATION: 051200J8

<400> SEQUENCE: 18
ggggaccact ttgtacaaga aagctggtta caaacacgtc gccattga                48

<210> SEQ ID NO 19
<211> LENGTH: 51
<212> TYPE: DNA
<213> ORGANISM: Artificial Sequence
<220> FEATURE:
<221> NAME/KEY: misc_feature
<223> OTHER INFORMATION: 051200J9

<400> SEQUENCE: 19
ggggacaagt ttgtacaaaa aagcaggacc atgttcaaat cggccgctgt g            51

<210> SEQ ID NO 20
<211> LENGTH: 42
```

```
<212> TYPE: DNA
<213> ORGANISM: Artificial Sequence
<220> FEATURE:
<221> NAME/KEY: misc_feature
<223> OTHER INFORMATION: 051200J10

<400> SEQUENCE: 20
ctgttgaact gggccgtcga gatgtttctc aggacctctt cg                    42

<210> SEQ ID NO 21
<211> LENGTH: 42
<212> TYPE: DNA
<213> ORGANISM: Artificial Sequence
<220> FEATURE:
<221> NAME/KEY: misc_feature
<223> OTHER INFORMATION: 051200J11

<400> SEQUENCE: 21
cgaagaggtc ctgagaaaca tctcgacggc ccagttcaac ag                    42

<210> SEQ ID NO 22
<211> LENGTH: 42
<212> TYPE: DNA
<213> ORGANISM: Artificial Sequence
<220> FEATURE:
<221> NAME/KEY: misc_feature
<223> OTHER INFORMATION: 051200J12

<400> SEQUENCE: 22
catcctgtat tcattcaaca acattggctc tggcgatgtg ac                    42

<210> SEQ ID NO 23
<211> LENGTH: 42
<212> TYPE: DNA
<213> ORGANISM: Artificial Sequence
<220> FEATURE:
<221> NAME/KEY: misc_feature
<223> OTHER INFORMATION: 051200J13

<400> SEQUENCE: 23
gtcacatcgc cagagccaat gttgttgaat gaatacagga tg                    42

<210> SEQ ID NO 24
<211> LENGTH: 42
<212> TYPE: DNA
<213> ORGANISM: Artificial Sequence
<220> FEATURE:
<221> NAME/KEY: misc_feature
<223> OTHER INFORMATION: 051200J14

<400> SEQUENCE: 24
agcggatata atattgacct ctacaattat ggctgccccc gg                    42

<210> SEQ ID NO 25
<211> LENGTH: 42
<212> TYPE: DNA
<213> ORGANISM: Artificial Sequence
<220> FEATURE:
<221> NAME/KEY: misc_feature
<223> OTHER INFORMATION: 051200J15

<400> SEQUENCE: 25
ccgggggcag ccataattgt agaggtcaat attatatccg ct                    42

<210> SEQ ID NO 26
<211> LENGTH: 48
<212> TYPE: DNA
```

```
<213> ORGANISM: Artificial Sequence
<220> FEATURE:
<221> NAME/KEY: misc_feature
<223> OTHER INFORMATION: 051200J16

<400> SEQUENCE: 26
ggggaccact tgtacaaga aagctggtca cgaacatgcg ctaatggg                    48

<210> SEQ ID NO 27
<211> LENGTH: 51
<212> TYPE: DNA
<213> ORGANISM: Artificial Sequence
<220> FEATURE:
<221> NAME/KEY: misc_feature
<223> OTHER INFORMATION: 051200J17

<400> SEQUENCE: 27
ggggacaagt ttgtacaaaa aagcaggacc atgcggagct ccctcgtgct g              51

<210> SEQ ID NO 28
<211> LENGTH: 42
<212> TYPE: DNA
<213> ORGANISM: Artificial Sequence
<220> FEATURE:
<221> NAME/KEY: misc_feature
<223> OTHER INFORMATION: 051200J18

<400> SEQUENCE: 28 tgcgcggcc tgttcgacga gcggttccgc aagatctgct cg                         42

<210> SEQ ID NO 29
<211> LENGTH: 42
<212> TYPE: DNA
<213> ORGANISM: Artificial Sequence
<220> FEATURE:
<221> NAME/KEY: misc_feature
<223> OTHER INFORMATION: 051200J19

<400> SEQUENCE: 29
cgagcagatc ttgcggaacc gctcgtcgaa caggccgcgc ca                        42

<210> SEQ ID NO 30
<211> LENGTH: 42
<212> TYPE: DNA
<213> ORGANISM: Artificial Sequence
<220> FEATURE:
<221> NAME/KEY: misc_feature
<223> OTHER INFORMATION: 051200J20

<400> SEQUENCE: 30
gtttctctat tcttttgaag attctggatt aggcgatgtt ac                        42

<210> SEQ ID NO 31
<211> LENGTH: 42
<212> TYPE: DNA
<213> ORGANISM: Artificial Sequence
<220> FEATURE:
<221> NAME/KEY: misc_feature
<223> OTHER INFORMATION: 051200J21

<400> SEQUENCE: 31
gtaacatcgc ctaatccaga atcttcaaaa gaatagagaa ac                        42

<210> SEQ ID NO 32
<211> LENGTH: 42
<212> TYPE: DNA
<213> ORGANISM: Artificial Sequence
```

-continued

```
<220> FEATURE:
<221> NAME/KEY: misc_feature
<223> OTHER INFORMATION: 051200J22

<400> SEQUENCE: 32
aatggataca atatcgacgt gttctcatat ggcgcgcccc gc                          42

<210> SEQ ID NO 33
<211> LENGTH: 42
<212> TYPE: DNA
<213> ORGANISM: Artificial Sequence
<220> FEATURE:
<221> NAME/KEY: misc_feature
<223> OTHER INFORMATION: 051200J23

<400> SEQUENCE: 33
gcggggcgcg ccatatgaga acacgtcgat attgtatcca tt                          42

<210> SEQ ID NO 34
<211> LENGTH: 48
<212> TYPE: DNA
<213> ORGANISM: Artificial Sequence
<220> FEATURE:
<221> NAME/KEY: misc_feature
<223> OTHER INFORMATION: 051200J24

<400> SEQUENCE: 34
ggggaccact ttgtacaaga aagctggcta atcacactct gaaatggg                    48

<210> SEQ ID NO 35
<211> LENGTH: 31
<212> TYPE: DNA
<213> ORGANISM: Artificial Sequence
<220> FEATURE:
<221> NAME/KEY: misc_feature
<223> OTHER INFORMATION: 142779

<400> SEQUENCE: 35
ttgaattgaa aatagattga tttaaaactt c                                      31

<210> SEQ ID NO 36
<211> LENGTH: 25
<212> TYPE: DNA
<213> ORGANISM: Artificial Sequence
<220> FEATURE:
<221> NAME/KEY: misc_feature
<223> OTHER INFORMATION: 142780

<400> SEQUENCE: 36
ttgcatgcgt aatcatggtc atagc                                             25

<210> SEQ ID NO 37
<211> LENGTH: 26
<212> TYPE: DNA
<213> ORGANISM: Artificial Sequence
<220> FEATURE:
<221> NAME/KEY: misc_feature
<223> OTHER INFORMATION: 140288

<400> SEQUENCE: 37
ttgaattcat gggtaataac tgatat                                            26

<210> SEQ ID NO 38
<211> LENGTH: 32
<212> TYPE: DNA
<213> ORGANISM: Artificial Sequence
<220> FEATURE:
```

```
<221> NAME/KEY: misc_feature
<223> OTHER INFORMATION: 142778

<400> SEQUENCE: 38
aaatcaatct attttcaatt caattcatca tt                           32

<210> SEQ ID NO 39
<211> LENGTH: 11
<212> TYPE: DNA
<213> ORGANISM: Artificial Sequence
<220> FEATURE:
<221> NAME/KEY: misc_feature
<223> OTHER INFORMATION: gtactaaaacc

<400> SEQUENCE: 39
gtactaaaac c                                                  11

<210> SEQ ID NO 40
<211> LENGTH: 11
<212> TYPE: DNA
<213> ORGANISM: Artificial Sequence
<220> FEATURE:
<221> NAME/KEY: misc_feature
<223> OTHER INFORMATION: ccgttaaattt

<400> SEQUENCE: 40
ccgttaaatt t                                                  11

<210> SEQ ID NO 41
<211> LENGTH: 45
<212> TYPE: DNA
<213> ORGANISM: Artificial Sequence
<220> FEATURE:
<221> NAME/KEY: misc_feature
<223> OTHER INFORMATION: 141223

<400> SEQUENCE: 41
ggatgctgtt gactccggaa atttaacggt ttggtcttgc atccc             45

<210> SEQ ID NO 42
<211> LENGTH: 14
<212> TYPE: DNA
<213> ORGANISM: Artificial Sequence
<220> FEATURE:
<221> NAME/KEY: misc_feature
<223> OTHER INFORMATION: atgcaatttaaact

<400> SEQUENCE: 42
atgcaattta aact                                               14

<210> SEQ ID NO 43
<211> LENGTH: 14
<212> TYPE: DNA
<213> ORGANISM: Artificial Sequence
<220> FEATURE:
<221> NAME/KEY: misc_feature
<223> OTHER INFORMATION: cggcaatttaacgg

<400> SEQUENCE: 43
cggcaattta acgg                                               14

<210> SEQ ID NO 44
<211> LENGTH: 44
<212> TYPE: DNA
<213> ORGANISM: Artificial Sequence
<220> FEATURE:
<221> NAME/KEY: misc_feature
```

```
<223> OTHER INFORMATION: 141222

<400> SEQUENCE: 44
ggtattgtcc tgcagacggc aatttaacgg cttctgcgaa tcgc                44

<210> SEQ ID NO 45
<211> LENGTH: 59
<212> TYPE: DNA
<213> ORGANISM: Artificial Sequence
<220> FEATURE:
<221> NAME/KEY: misc_feature
<223> OTHER INFORMATION: 051199J1

<400> SEQUENCE: 45
cctctagatc tcgagctcgg tcaccggtgg cctccgcggc cgctggatcc ccagttgtg    59

<210> SEQ ID NO 46
<211> LENGTH: 33
<212> TYPE: DNA
<213> ORGANISM: Artificial Sequence
<220> FEATURE:
<221> NAME/KEY: misc_feature
<223> OTHER INFORMATION: 1298TAKA

<400> SEQUENCE: 46
gcaagcgcgc gcaatacatg gtgttttgat cat                           33

<210> SEQ ID NO 47
<211> LENGTH: 30
<212> TYPE: DNA
<213> ORGANISM: Artificial Sequence
<220> FEATURE:
<221> NAME/KEY: misc_feature
<223> OTHER INFORMATION: 177996

<400> SEQUENCE: 47
gaatgacttg gttgacgcgt caccagtcac                               30

<210> SEQ ID NO 48
<211> LENGTH: 25
<212> TYPE: DNA
<213> ORGANISM: Artificial Sequence
<220> FEATURE:
<221> NAME/KEY: misc_feature
<223> OTHER INFORMATION: 135640

<400> SEQUENCE: 48
cttattagta ggttggtact tcgag                                    25

<210> SEQ ID NO 49
<211> LENGTH: 37
<212> TYPE: DNA
<213> ORGANISM: Artificial Sequence
<220> FEATURE:
<221> NAME/KEY: misc_feature
<223> OTHER INFORMATION: 135638

<400> SEQUENCE: 49
gtccccagag tagtgtcact atgtcgaggc agttaag                       37

<210> SEQ ID NO 50
<211> LENGTH: 64
<212> TYPE: DNA
<213> ORGANISM: Artificial Sequence
<220> FEATURE:
<221> NAME/KEY: misc_feature
<223> OTHER INFORMATION: 080399J19
```

<400> SEQUENCE: 50
gtatgtccct tgacaatgcg atgtatcaca tgatataatt actagcaagg gaagccgtgc    60
ttgg                                                                 64

<210> SEQ ID NO 51
<211> LENGTH: 18
<212> TYPE: DNA
<213> ORGANISM: Artificial Sequence
<220> FEATURE:
<221> NAME/KEY: misc_feature
<223> OTHER INFORMATION: HL 2
<220> FEATURE:
<221> NAME/KEY: modified_base
<222> LOCATION: (1)..(18)
<223> OTHER INFORMATION: i
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 51
wsngcngcng cntaytgy                                                  18

<210> SEQ ID NO 52
<211> LENGTH: 28
<212> TYPE: DNA
<213> ORGANISM: Artificial Sequence
<220> FEATURE:
<221> NAME/KEY: misc_feature
<223> OTHER INFORMATION: HL 12
<220> FEATURE:
<221> NAME/KEY: modified_base
<222> LOCATION: (1)..(28)
<223> OTHER INFORMATION: i
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 52

```
ggnacnrkrt crttnnnrtg ngtnaync                           28

<210> SEQ ID NO 53
<211> LENGTH: 26
<212> TYPE: DNA
<213> ORGANISM: Artificial Sequence
<220> FEATURE:
<221> NAME/KEY: misc_feature
<223> OTHER INFORMATION: HL 6
<220> FEATURE:
<221> NAME/KEY: modified_base
<222> LOCATION: (1)..(26)
<223> OTHER INFORMATION: i
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 53
avngcnccnc cnarnswrtg nccngt                             26
```

LIPOLYTIC ENZYME GENES

CROSS-REFERENCE TO RELATED APPLICATIONS

This application is a continuation of U.S. application Ser. No. 10/250,824 filed Jul. 2, 2003, which is a 35 U.S.C. 371 national application of PCT/DK02/00124 filed 25 Feb. 2002, which claims priority or the benefit under 35 U.S.C. 119 of Danish application no. PA 2001 00304 filed 23 Feb. 2001 and U.S. provisional application No. 60/271,385 filed 26 Feb. 2001, the contents of which are fully incorporated herein by reference.

FIELD OF THE INVENTION

The present invention relates to a method of generating diversity into lipolytic enzymes by the use of the so-called family shuffling of homologous genes. The invention also relates to polynucleotides for use in the method, and to lipolytic enzymes encoded by the polynucleotides.

BACKGROUND OF THE INVENTION

The lipase of *Thermomyces lanuginosus* (also known as *Humicola lanuginosa*) is known to be useful for various industrial purposes such as detergents and baking (EP 258068, WO 9404035). Its amino acid and DNA sequences are shown in U.S. Pat. No. 5,869,438.

The prior art describes the modification of the amino acid sequence of the *T. lanuginosus* lipase to create variants with the aim of modifying the enzyme properties. Thus, U.S. Pat. No. 5,869,438, WO 95/22615, WO 97/04079 and WO 00/32758 disclose the use of mutagenesis of the lipase gene to produce such variants. WO 00/32758 also discloses the construction of variants with the backbone from *T. lanuginosus* lipase and C-terminal from *Fusarium oxysporum* phospholipase by PCR reaction.

Crameri et al., Nature, 391: 288-291 (1998) discloses DNA shuffling of a family of naturally occurring homologous genes from diverse species to create diversity into proteins. U.S. Pat. No. 6,159,687 discloses shuffling of genes encoding variants of the *T. lanuginosus* lipase. WO 98/41623 discloses shuffling of heterologous polynucleotide sequences.

The following published sequences of lipolytic enzymes from *Aspergillus* have amino acid identities of 49-51% to the *T. lanuginosus* lipase: Lysophospholipase from *A. foetidus* (EMBL A93428, U.S. Pat. No. 6,140,094), lipase from *A. tubingensis* (EMBL A84589, WO 9845453), phospholipase A1 from *A. oryzae* (EMBL E16314, EP 575133, JP 10155493 A) and Lysophospholipase from *A. niger* (EMBL A90761, WO 98/31790).

R. Lattmann et al., Biocatalysis, 3 (1-2): 137-144 (1990) disclose an esterase from *Talaromyces thermophilus*. V. W. Ogundero, Mycologia, 72 (1): 118-126 (1980) describes the lipase activity of *Talaromyces thermophilus*. U.S. Pat. No. 4,275,011 and EP 258068 refer to a lipase from *Thermomyces ibadanensis*. B. A. Oso, Canadian Journal of Botany, 56: 1840-1843 (1978) describes the lipase activity of *Talaromyces emersonii*.

SUMMARY OF THE INVENTION

The inventors have isolated novel lipolytic enzyme genes with a high homology to the *T. lanuginosus* lipase gene and are thus well suited for use in gene shuffling. The novel genes are shown as SEQ ID NO: 3, 5, 7, 9 and 11. Identity tables for some protein and DNA sequences are shown below. The novel sequences are identified as follows:

Talthe1M: SEQ ID NO: 3 and 4 from *Talaromyces thermophilus*.
Theiba1M: SEQ ID NO: 5 and 6 from *Thermomyces ibadanensis*.
Taleme1M: SEQ ID NO: 7 and 8 from *Talaromyces emersonii*.
Talbys1M: SEQ ID NO: 9 and 10 from *Talaromyces byssochlamydoides*.

The following known sequences are included for comparison:

Thelan1M: Lipase from *Thermomyces lanuginosus*, SEQ ID NO: 1 and 2.
Asptub2M: EMBL A84589 Lipase from *Aspergillus tubingensis*.
Aspory3M: EMBL E16314 Phospholipase A1 from *Aspergilus oryzae*.
Aspnig2M: EMBL A90761 Lysophospholipase from *Aspergillus niger*.

The following is an identity table of the mature proteins:

|          | Thelan1 | Talthe1 | Theiba1 | Taleme1 | Talbys1 | Asptub2 | Aspory3 | Aspnig2 |
|----------|---------|---------|---------|---------|---------|---------|---------|---------|
| Thelan1M | 100.0   | 88.1    | 78.1    | 61.9    | 57.4    | 50.6    | 50.4    | 49.1    |
| Talthe1M | 88.1    | 100.0   | 78.8    | 61.5    | 59.2    | 48.7    | 47.8    | 48.0    |
| Theiba1M | 78.1    | 78.8    | 100.0   | 61.8    | 58.0    | 49.4    | 50.4    | 48.0    |
| Taleme1M | 61.9    | 61.5    | 61.8    | 100.0   | 83.1    | 54.8    | 56.1    | 53.7    |
| Talbys1M | 57.4    | 59.2    | 58.0    | 83.1    | 100.0   | 50.9    | 54.9    | 49.1    |
| Asptub2M | 50.6    | 48.7    | 49.4    | 54.8    | 50.9    | 100.0   | 55.9    | 93.7    |
| Aspory3M | 50.4    | 47.8    | 50.4    | 56.1    | 54.9    | 55.9    | 100.0   | 53.7    |
| Aspnig2M | 49.1    | 48.0    | 48.0    | 53.7    | 49.1    | 93.7    | 53.7    | 100.0   |

The following is an identity table of DNA sequences coding for the mature proteins (stop codons omitted):

|  | Thelan1 | Talthe1 | Theiba1 | Taleme1 | Talbys1 | Asptub2 | Aspory3 | Aspnig2 |
|---|---|---|---|---|---|---|---|---|
| Thelan1M | 100.0 | 86.0 | 79.3 | 62.0 | 58.4 | 57.0 | 55.6 | 56.2 |
| Talthe1M | 86.0 | 100.0 | 79.1 | 62.6 | 60.0 | 57.8 | 55.7 | 57.1 |
| Theiba1M | 79.3 | 79.1 | 100.0 | 63.5 | 60.4 | 56.6 | 57.8 | 55.6 |
| Taleme1M | 62.0 | 62.6 | 63.5 | 100.0 | 84.1 | 58.2 | 58.4 | 58.7 |
| Talbys1M | 58.4 | 60.0 | 60.4 | 84.1 | 100.0 | 57.5 | 56.5 | 56.8 |
| Asptub2M | 57.0 | 57.8 | 56.6 | 58.2 | 57.5 | 100.0 | 58.7 | 91.7 |
| Aspory3M | 55.6 | 55.7 | 57.8 | 58.4 | 56.5 | 58.7 | 100.0 | 56.5 |
| Aspnig2M | 56.2 | 57.1 | 55.6 | 58.7 | 56.8 | 91.7 | 56.5 | 100.0 |

Accordingly, the invention provides a method of generating genetic diversity into lipolytic enzymes by family shuffling of two or more homologous genes which encode lipolytic enzymes. One gene encodes a lipolytic enzyme with at least 90% identity to the *T. lanuginosus* lipase, and another gene encodes a lipolytic enzyme with 55-90% identity to the *T. lanuginosus* lipase. The DNA shuffling technique is used to create a library of chimeric shuffled genes, and this is expressed in a suitable expression system and the expressed proteins are screened for lipolytic enzyme activity. The expressed proteins may further be screened to identify lipolytic enzymes with improved properties.

The invention also provides a polynucleotide comprising a nucleotide sequence encoding a lipolytic enzyme and a lipolytic enzyme (a polypeptide with lipolytic enzyme activity).

The polynucleotide may be a DNA sequence cloned into a plasmid present in *E. coli* deposit number DSM 14047, 14048, 14049, or 14051, the DNA sequence encoding a mature peptide shown in SEQ ID NO: 3, 5, 7 or 9 or one that can be derived therefrom by substitution, deletion, and/or insertion of one or more nucleotides. The polynucleotide may have at least 90% identity with the DNA sequence encoding a mature peptide shown in SEQ ID NO: 3, at least 80% identity with the DNA sequence encoding a mature peptide shown in SEQ ID NO: 5, at least 65% identity with the DNA sequence encoding a mature peptide shown in SEQ ID NO: 7, or at least 60% identity with the DNA sequence encoding a mature peptide shown in SEQ ID NO: 9. It may also be an allelic variant of the DNA sequence encoding a mature peptide shown in SEQ ID NO: 3, 5, 7 or 9; or it may hybridize under high stringency conditions with a complementary strand of the nucleic acid sequence encoding a mature peptide shown in SEQ ID NO: 3, 5, 7 or 9, or a subsequence thereof having at least 100 nucleotides.

The lipolytic enzyme may be encoded by a DNA sequence cloned into a plasmid present in *E. coli* deposit number DSM 14047 or 14049, or may have an amino acid sequence which is the mature peptide of SEQ ID NO: 6 or 10, or one that can be derived therefrom by substitution, deletion, and/or insertion of one or more amino acids. The lipolytic enzyme may have an amino acid sequence which has at least 80% identity with the mature peptide of SEQ ID NO: 6 or at least 60% identity with the mature peptide of SEQ ID NO: 10. The lipolytic enzyme may further be immunologically reactive with an antibody raised against the mature peptide of SEQ ID NO: 6 or 10 in purified form, be an allelic variant of the mature peptide of SEQ ID NO: 6 or 10; or be encoded by a nucleic acid sequence which hybridizes under high stringency conditions with a complementary strand of the nucleic acid sequence encoding a mature peptide shown in SEQ ID NO: 5 or 9, or a subsequence thereof having at least 100 nucleotides.

BRIEF DESCRIPTION OF DRAWINGS

FIG. 1 shows a PCR scheme used in Example 7.

DETAILED DESCRIPTION OF THE INVENTION

Genomic DNA Source

Lipolytic enzyme genes of the invention may be derived from strains of *Talaromyces* or *Thermomyces*, particularly *Talaromyces thermophilus*, *Thermomyces ibadanensis*, *Talaromyces emersonii* or *Talaromyces byssochlamydoides*, using probes designed on the basis of the DNA sequences in this specification.

Thus, genes and polypeptides shown in the sequence listing were isolated from the organisms indicated below. Strains of *Escherichia coli* containing the genes were deposited by the inventors under the terms of the Budapest Treaty with the DSMZ—Deutsche Sammlung von Microorganismen und Zellkulturen GmbH, Mascheroder Weg 1b, D-38124 Braunschweig DE as follows:

| Source organism | Gene and polypeptide sequences | Clone deposit No. | Clone deposit date |
|---|---|---|---|
| *Talaromyces thermophilus* ATCC 10518 | SEQ ID NOS: 3 and 4 | DSM 14051 | 8 Feb. 2001 |
| *Thermomyces ibadanensis* CBS 281.67 = ATCC 22716 | SEQ ID NOS: 5 and 6 | DSM 14049 | 8 Feb. 2001 |
| *Talaromyces emersonii* UAMH 5005 = NRRL 3221 = ATCC 16479 = IMI 116815 = CBS 393.64 | SEQ ID NOS: 7 and 8 | DSM 14048 | 8 Feb. 2001 |

| Source organism | Gene and polypeptide sequences | Clone deposit No. | Clone deposit date |
|---|---|---|---|
| *Talaromyces byssochlamydoides* CBS 413.71 = IMI 178524 = NRRL 3658 | SEQ ID NOS: 9 and 10 | DSM 14047 | 8 Feb. 2001 |

The above source organisms are freely available on commercial terms from the following strain collections:

ATCC (American Type Culture Collection), 10801 University Boulevard, Manassas, Va. 20110-2209, USA.

CBS (Centraalbureau voor Schimmelcultures), Uppsalalaan 8, 3584 CT Utrecht, The Netherlands.

UAMH (University of Alberta Mold Herbarium & Culture Collection), Devonian Botanic Garden, Edmonton, Alberta, Canada T6G 3GI.

IMI: International Mycological Institute, Bakeham Lane, Englefield Green, EGHAM, Surrey TW20 9TY, United Kingdom.

Polynucleotides

The polynucleotides to be used for recombination (shuffling) are two or more genes encoding lipolytic enzymes, including one with at least 90% identity and one with 55-90% identity to the *T. lanuginosus* lipase (SEQ ID NO: 2). The poloynucleotides differ in at least one nucleotide.

The starting material may include the mature part of two or more (e.g., three, four or five) of SEQ ID NO: 1, 3, 5, 7 and/or 9. It may also include genes encoding two or more (e.g., three, four or five) of variants of SEQ ID NO: 2, 4, 6, 8 or 10 obtained by deleting, substituting and/or inserting one or more amino acids and/or by attaching a peptide extension at the N- and/or C- terminal C-terminal. Examples of variants of the *T. lanuginosus* lipase are described, e.g., in U.S. Pat. No. 5,869,438, WO 9522615, WO 9704079 and WO 0032758, and similar variants can be made by altering corresponding amino acids in the other sequences.

Any introns present in the genes may optionally be removed before the shuffling.

DNA Recombination (Shuffling)

Shuffling between two or more homologous input polynucleotides (starting-point polynucleotides) may involve fragmenting the polynucleotides and recombining the fragments, to obtain output polynucleotides (i.e., polynucleotides that have been subjected to a shuffling cycle) wherein a number of nucleotide fragments are exchanged in comparison to the input polynucleotides.

DNA recombination or shuffling may be a (partially) random process in which a library of chimeric genes is generated from two or more starting genes. A number of known formats can be used to carry out this shuffling or recombination process.

The process may involve random fragmentation of parental DNA followed by reassembly by PCR to new full length genes, e.g., as presented in U.S. Pat. No. 5,605,793, U.S. Pat. No. 5,811,238, U.S. Pat. No. 5,830,721, U.S. Pat. No. 6,117,679. In-vitro recombination of genes may be carried out, e.g., as described in U.S. Pat. No. 6,159,687, WO 98/41623, U.S. Pat. No. 6,159,688, U.S. Pat. No. 5,965,408, U.S. Pat. No. 6,153,510. The recombination process may take place in vivo in a living cell, e.g., as described in WO 97/07205 and WO 98/28416.

The parental DNA may be fragmented by DNA'se I treatment or by restriction endonuclease digests as described by Kikuchi et al. (Gene 236:159-167 (2000)). Shuffling of two parents may be done by shuffling single stranded parental DNA of the two parents as described in Kikuchi et al. (Gene 243:133-137 (2000)).

A particular method of shuffling is to follow the methods described in Crameri et al., Nature, 391: 288-291 (1998) and Ness et al., Nature Biotechnology 17: 893-896. Another format would be the methods described in U.S. Pat. No. 6,159,687: Examples 1 and 2.

Properties of Lipolytic Enzyme

The lipolytic enzyme obtained by the invention is able to hydrolyze carboxylic ester bonds and is classified as EC 3.1.1 according to Enzyme Nomenclature 1992, Academic Press, Inc. It may particularly have activity as a lipase (triacylglycerol lipase) (EC 3.1.1.3), phospholipase A1 (EC 3.1.1.32), phospholipase A2 (EC 3.1.1.4), cholesterol esterase (EC 3.1.1.13) and/or galactolipase (EC 3.1.1.26).

The thermostability was evaluated by means of Differential Scanning Calorimetry (DSC). The denaturation peak ($T_d$) when heated at 90 deg/hr at pH 5 is slightly above 75° C. for the lipolytic enzyme from *T. ibadanensis*, compared to slightly above 70° C. for the prior-art *T. lanuginosus* lipase. The lipolytic enzyme from *T. ibadanensis* has optimum activity at alkaline pH (similar to the *T. lanuginosus* lipase) and has an isoelectric point of about 4.3 (slightly lower than the *T. lanuginosus* lipase).

Homology and Alignment

The best alignment of the mature parts of SEQ ID NOS: 2, 4, 6, 8 and 10 is achieved by inserting a gap of one amino acid between Q249 and P/G250 of SEQ ID NOS: 2, 4 and 6. This alignment defines corresponding amino acids.

The degree of homology may be determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman and Wunsch, 1970, Journal of Molecular Biology, 48: 443-45), using GAP with the following settings for polypeptide sequence comparison: GAP creation penalty of 3.0 and GAP extension penalty of 0.1.

The determination of homology may also be made using Align from the fasta package version v20u6. Align is a Needleman-Wunsch alignment (i.e., global alignment), useful for both protein and DNA alignments. The default scoring matrices BLOSUM50 and the identity matrix are used for protein and DNA alignments respectively. The penalty for the first residue in a gap is −12 for proteins and −16 for DNA. While the penalty for additional residues in a gap is −2 for proteins and −4 for DNA.

The homologies discussed in this specification may correspond to at least 60% identity, in particular to at least 70% or at least 80% identity, e.g., at least 90% or at least 95% identity.

Use of Lipolytic Enzyme

Depending on the substrate specificity, the enzyme of the invention can be used, e.g., in filtration improvement, vegetable oil treatment, baking, detergents, or preparation of lysophospholipid. Thus, it may be used in known applications of lipolytic enzymes by analogy with the prior art, e.g.:

In the pulp and paper industry, to remove pitch or to remove ink from used paper. WO 92/13130, WO 92/07138, JP 2160984 A, EP 374700.

Baking. WO 94/04035, WO 00/32758.

Detergents. WO 97/04079, WO 97/07202, WO 97/41212, WO 98/08939 and WO 97/43375.

Leather industry. GB 2233665, EP 505920.

An enzyme with lipase activity may be used for fat hydrolysis and for modification of triglycerides and for production of mono- and diglycerides.

An enzyme with lipase activity may be used for interesterification of bulk fats, production of frying fats, shortenings and margarine components.

An enzyme with phospholipase activity (A1, A2) may be used for degumming of vegetable oils and for lysophospholipid production.

Improvement of Filtration

An enzyme with lysophospholipase activity can be used to improve the filterability of an aqueous solution or slurry of carbohydrate origin by treating it with the variant. This is particularly applicable to a solution or slurry containing a starch hydrolyzate, especially a wheat starch hydrolyzate since this tends to be difficult to filter and to give cloudy filtrates. The treatment can be done in analogy with EP 219,269 (CPC International).

Detergents

The lipolytic enzyme produced by the invention may be used as a detergent additive, e.g., at a concentration (expressed as pure enzyme protein) of 0.001-10 (e.g., 0.01-1) mg per gram of detergent or 0.001-100 (e.g., 0.01-10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK98/08939 and WO 97/43375.

The detergent composition of the invention may particularly be formulated for hand or machine dishwashing operations. e.g., as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight, e.g., 0.5-40%, such as 1-30%, typically 1.5-20%.

Dough and Baked Products

The lipolytic enzyme can be used in the preparation of dough and baked products made from dough, such as bread and cakes, e.g., to increase dough stability and dough handling properties, or to improve the elasticity of the bread or cake. Thus, it can be used in a process for making bread, comprising adding it to the ingredients of a dough, kneading the dough and baking the dough to make the bread. This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.) or EP 426211 (Unilever). The lipolytic enzyme may be used together with an anti-staling amylase, particularly an endo-amylase such as a maltogenic amylase in analogy with WO 99/53769 (Novo Nordisk). Thus, the lipolytic enzyme may be incorporated in a flour composition such as a dough or a premix for dough.

MATERIALS AND METHODS

Strains and Plasmids:

Plasmid pMT2188

The *Aspergillus oryzae* expression plasmid pCaHj483 (WO 98/00529) consists of an expression cassette based on the *Aspergillus niger* neutral amylase II promoter fused to the *Aspergillus nidulans* triose phosphate isomerase non translated leader sequence (Pna2/tpi) and the *A. niger* amyloglycosidase terminator (Tamg). Also present on the plasmid is the *Aspergillus* selective marker amdS from *A. nidulans* enabling growth on acetamide as sole nitrogen source. These elements are cloned into the *E. coli* vector pUC19 (New England Biolabs). The ampicillin resistance marker enabling selection in *E. coli* of this plasmid was replaced with the URA3 marker of *Saccharomyces cerevisiae* that can complement a pyrF mutation in *E. coli*, the replacement was done in the following way:

The pUC19 origin of replication was PCR amplified from pCaHj483 with the primers 142779 (SEQ ID NO: 35) and 142780 (SEQ ID NO: 36).

Primer 142780 introduces a BbuI site in the PCR fragment. The Expand PCR system (Roche Molecular Biochemicals, Basel, Switzerland) was used for the amplification following the manufacturers instructions for this and the subsequent PCR amplifications.

The URA3 gene was amplified from the general *S. cerevisiae* cloning vector pYES2 (Invitrogen corporation, Carlsbad, Calif., USA) using the primers 140288 (SEQ ID NO: 37) and 142778 (SEQ ID NO: 38).

Primer 140288 introduces an EcoRI site in the PCR fragment. The two PCR fragments were fused by mixing them and amplifying using the primers 142780 and 140288 in the splicing by overlap method (Horton et al., Gene, 77:61-68 (1989)).

The resulting fragment was digested with EcoRI and BbuI and ligated to the largest fragment of pCaHj 483 digested with the same enzymes. The ligation mixture was used to transform the pyrF *E. coli* strain DB6507 (ATCC 35673) made competent by the method of Mandel and Higa (Mandel and Higa, J. Mol. Biol. 45: 154 (1970)). Transformants were selected on solid M9 medium (Sambrook et al., Molecular Cloning, A Laboratory Manual, 2nd edition, Cold Spring Harbor Laboratory Press (1989)) supplemented with 1 g/l casaminoacids, 500 micrograms/l thiamine and 10 mg/l kanamycin.

A plasmid from a selected transformant was termed pCaHj527. The Pna2/tpi promoter present on pCaHj527 was subjected to site directed mutagenesis by a simple PCR approach.

Nucleotides 134-144 were altered from SEQ ID NO: 39 to SEQ ID NO: 40 using the mutagenic primer 141223 (SEQ ID NO: 41).

Nucleotides 423-436 were altered from SEQ ID NO: 42 to SEQ ID NO: 43 using the mutagenic primer 141222 (SEQ ID NO: 44).

The resulting plasmid was termed pMT2188.

Plasmid pENI1861

Plasmid pENI1861 was made in order to have the state of the art *Aspergillus* promoter in the expression plasmid, as well as a number of unique restriction sites for cloning.

A PCR fragment (app. 620 bp) was made using pMT2188 (see above) as template and the primers 051199J1 (SEQ ID 45) and 1298TAKA (SEQ ID NO: 46).

The fragment was cut BssHII and BgI II, and cloned into pENI1849 which was also cut with BssHII and BgI II. The cloning was verified by sequencing. Plasmid pENI1902 was made in order to have a promoter that works in both *E. coli* and *Aspergillus*. This was done by unique site elimination using the "Chameleon double stranded site-directed mutagenesis kit" as recommended by Stratagene®.

Plasmid pENI1861

Plasmid pENI1861 was used as template and the following primers with 5' phosphorylation were used as selection primers: 177996 (SEQ ID NO: 47), 135640 (SEQ ID NO: 48) and 135638 (SEQ ID NO: 49).

The 080399J19 primer (SEQ ID NO: 50) with 5' phosphorylation was used as mutagenic primer to introduce a −35 and −10 promoter consensus sequence (from *E. coli*) in the *Aspergillus* expression promoter. Introduction of the mutations was verified by sequencing.

Plasmid pENI1960

Plasmid pENI1960 was made using the Gateway Vector™ conversion system (Lifetechnology® cat no. 11828-019) by cutting pENI1902 with BamHI, filling the DNA ends using Klenow fragment polymerase and nucleotides (thus making blunt ends) followed by ligation to reading frame A Gateway™ PCR fragment. The cloning in the correct orientation was confirmed by sequencing.

Media and Substrates

YPG: 4 g/L Yeast extract, 1 g/L $KH_2PO_4$, 0.5 g/L $MgSO_4$-7aq, 5 g/L Glucose, pH 6.0.

EXAMPLES

Example 1

Plasmids Harboring Lipolytic Enzyme Genes

Genomic DNA Preparation

Strains of *Thermomyces ibadanensis, Talaromyces emersonii, Talaromyces byssochlamydoides,* and *Talaromyces thermophilus* were used as a genomic DNA supplier. Each strain was cultivated in 100 ml of YPG at appropriate temperature for several days. Mycelia was harvested and ground in liquid $N_2$. It was suspended with 2 ml of 50 mM Tris-HCl (pH8.0) buffer including 100 mM NaCl, 25 mM EDTA, and 1% SDS and then 12 microliters of proteinase K (25 mg/ml) was added. The suspension was incubated at 65° C. for 30-60 min. Phenol extraction was done to remove proteins and DNA was precipitated by 0.7 volume of isopropanol. The precipitate was dissolved with sterilized water and RNase was added. After Phenol/isoamylalcohol extraction, DNA was precipitated by EtOH.

PCR Screening of Lipolytic Enzyme Genes

PCR reactions on each genomic DNA were done with HL2 and HL12 (SEQ ID NOS: 51 and 52) or HL2 and HL6 (SEQ ID NOS: 51 and 53) designed based upon alignment lipases.

Reaction components (2.6 ng/microliter of genomic DNA, 250 mM dNTP each, primer 250 nM each, 0.1 U/microliter of Taq polymerase in 1× buffer (Roche Diagnostics, Japan)) were mixed and submitted for PCR under the following conditions.

| Step | Temperature | Time |
|---|---|---|
| 1 | 94° C. | 1 min |
| 3 | 50° C. | 1 min |
| 4 | 72° C. | 2 min |
| 5 | 72° C. | 10 min |
| 6 | 4° C. | forever |

Steps 1 to 3 were repeated 30 times.

540 bp of fragment and 380 bp of fragment were amplified from primer sets of HL2/HL12 and HL2/HL6, respectively. They were gel-purified with GFX™ PCR DNA and Gel Band Purification kit (Amersham Pharmacia Biotech). Each DNA was sequenced and compared to the lipase, showing that a clone encodes the internal part of the lipase.

Cloning of Lipase Genes

All lipase genes were cloned using LA PCR™ in vitro Cloning Kit (TaKaRa) according to the manufacturer's instructions. Thus, genomic DNA was cut with various restriction enzymes and each DNA was ligated with the appropriate cassette of the kit. Each ligation solution was applied to PCR with the primers of the one designed from internal sequence and a cassette primer of the kit. Amplified DAN fragment was sequenced. This step was repeated till ORF was determined.

The fidelity of LA- taq polymerase of the kit is not good so in order to get the right sequence whole gene was amplified by Expand high fidelity polymerase according to the manufacturer's instructions.

Amplified DNA fragment was gel-purified with GFX™ PCR DNA and Gel Band Purification kit (Amersham Pharmacia Biotech) and ligated into a pT7Blue vector or pST BLue-1 AccepTor vector (Novagen) with ligation high (TOYOBO, Japan). The ligation mixtures were transformed into *E. coli* JM109 or DH5α. The sequence of four plasmids of each gene was determined and their sequences were compared. The sequence of majority is defined as the right nucleotide sequence.

Example 2

Cloning of Lipase into *Aspergillus* Expression Vector 3 different PCR reaction were run using PWO polymerase in the following reaction 94° C. 5 min, 30* (94° C. 30 sec., 50° C. 30 sec, 72° C. 2 min, 72° C. 5 min). In each case, the template was a plasmid harboring a lipolytic enzyme gene prepared as in Example 1, and the following primers were used:

A: Plasmid with gene from *Talaromyces thermophilus* and oligo 051200j1/051200j8 (SEQ ID NOS: 11 and 18).

B: Plasmid with gene from *Talaromyces emersonii* and oligo 051200j9/051200j16 (SEQ ID NOS: 19 and 26).

C: Plasmid with gene from *Thermomyces Ibadanensis* and oligo 051200j17/051200j24 (SEQ ID NOS: 27 and 34).

The PCR fragments were run and purified from a 1% agarose gel and cloned into pENI1960 (see above) using Gateway cloning as recommended by the supplier (Life Technologies) and transformed into *E. coli* DH10b (Life Technologies, Gaithersburg, Md.) and sequenced, thus creating pENI 2146 (*Talaromyces emersonii* lipase gene), pENI2147 (*Thernomyces Ibadanensis* lipase gene) and pENI2148 (*Talaromyces thermophilus* lipase gene).

These were transformed into JaI250 (described in WO 00/39322) and lipase activity identified as mentioned in WO 00/24883.

Example 3

Construction of Intron-Less Lipase Genes

Removal of Introns from *Talaromyces thermophilus* Lipase Gene

4 PCR reactions were run using PWO polymerase and pENI2148 as template (94° C. 5 min, 30* (94° C. 30 sec., 50° C. 30 sec, 72° C. 1 min), 72° C. 5 min) and the following oligos:

1: 051200j1 and 051200j3 (SEQ ID NOS: 11 and 13)
2: 051200j2 and 051200j5 (SEQ ID NOS: 12 and 15)
3: 051200j4 and 051200j7 (SEQ ID NOS: 14 and 17)
4: 051200j6 and 051200j8 (SEQ ID NOS: 16 and 18)

The specific bands were run and purified from a 1.5% agarose gel. Equal amounts of PCR fragments were mixed along with PWO polymerase, buffer, dNTP, oligo 051200j1 and 051200j8 (SEQ ID NO: 11 and 18, total of 50 microliters, as recommended by the supplier Boehringer Mannheim) and a second PCR was run (94° C. 5 min, 30* (94° C. 30 sec., 50° C. 30 sec, 72° C. 2 min), 72° C. 5 min).

The correct band size was checked on a 1.5% agarose gel (app. 900 bp) and the rest of the PCR-fragment was purified using Biorad spin columns (cat no.732-6225)

The PCR-fragment was cloned into pENI1960 cut with ScaI (in order to cleave in the ccdB gene) using Gateway cloning as recommended by the supplier (Life Technologies) and transformed into *E. coli* DH10b and sequenced, thus creating intron-less *Talaromyces thermophilus* lipase gene.

Removal of Introns from *Talaromyces emersonii* LiPase Gene

4 PCR reactions were run using PWO polymerase and pENI2146 as template (94° C. 5 min, 30* (94° C. 30 sec., 50° C. 30 sec, 72° C. 1 min), 72° C. 5 min)

1: 051200j9 and 051200j11 (SEQ ID NOS: 19 and 21).
2: 051200j10 and 051200j13 (SEQ ID NOS: 20 and 23).
3: 051200j12 and 051200j15 (SEQ ID NOS: 22 and 25).
4: 051200j14 and 051200j16 (SEQ ID NOS: 24 and 26).

The specific bands were run and purified from a 1.5% agarose gel. Equal amounts of PCR fragments were mixed along with PWO polymerase, buffer, dNTP, oligo 051200j9 and 051200j16 (SEQ ID NOS: 19 and 26, total of 50 microliters, as recommended by the supplier) and a second PCR was run (94° C. 5 min, 30* (94° C. 30 sec., 50° C. 30 sec, 72° C. 5 min).

The correct band size was checked on a 1.5% agarose gel (app. 900 bp) and the rest of the PCR-fragment was purified using Biorad spin columns.

The PCR-fragment was cloned into and cloned into pENI1960 cut ScaI using Gateway cloning as recommended by the supplier (Life Technologies) and transformed into *E. coli* DH10b and sequenced, thus creating an intron-less *Talaromyces emersonii* lipase gene.

Removal of Introns from *Thermomyces Ibadanensis* Lipase Gene

4 PCR reactions were run using PWO polymerase and pENI2147 as template (94° C. 5 min, 30* (94° C. 30 sec., 50° C. 30 sec, 72° C. 1 min), 72° C. 5 min)

1: 051200j17 and 051200j19 (SEQ ID NOS: 27 and 29).
2: 051200j18 and 051200j21 (SEQ ID NOS: 28 and 31).
3: 051200j20 and 051200j23 (SEQ ID NOS: 30 and 33).
4: 051200j22 and 051200j24 (SEQ ID NOS: 32 and 34).

The specific bands were run and purified from a 1.5% agarose gel. Equal amounts of PCR fragments were mixed along with PWO polymerase, buffer, dNTP, oligo 051200j17 and 051200j24 (SEQ ID NO: 27 and 34, total of 50 microliters, as recommended by the supplier) and a second PCR was run (94° C. 5 min, 30* (94° C. 30 sec., 50° C. 30 sec, 72°min).

The correct band size was checked on a 1.5% agarose gel (app. 900 bp) and the rest of the PCR-fragment was purified using Biorad spin columns The PCR-fragment was cloned into and cloned into pENI1960 cut ScaI using Gateway cloning as recommended by supplier (life technologies) and transformed into *E. coli* DH10b and sequenced, thus creating intron-less *Thermomyces Ibadanensis* lipase gene.

Example 4

Shuffling of Lipolytic Enzyme Genes

Plasmids containing DNA sequences encoding lipolytic enzymes are mixed in equimolar amounts. The following components where mixed in a microtube:

2 microliters plasmid mixture (0.15 microgram/microliter), specific primers flanking the gene (1 pmol/µ), 2 microliters 2.5 mM dNTP, 2.5 mM MgCl2, 2 µl 10* taq buffer (Perkin Elmer), 0.5 microliter taq enzyme in a total volume of 20 microliters.

The tube is set in a Perkin Elmer 2400 thermocycler. The following PCR-program is run:(94° C., 5 minutes) 1 cycle:

(94° C., 30 seconds, 70° C., 0 seconds) 99 cycles(72° C., 2 minutes, 4°

The PCR-reaction is run on a 1.5% agarose gel. A DNA-band of the specific expected size is cut out of the agarose gel and purified using JETsorb (from GENOMED Inc.). The purified PCR-product is cloned into a TA-vector (from Invitrogen (the original TA cloning kit). The ligated product is transformed into a standard *Escherichia coli* strain (DH5a).

The shuffled sequences can then be subcloned from the *E. coli* TA vector into the yeast vector pJSOO26 (WO 99/28448) as a BamHI-XbaI fragment (see WO 97/07205), and e.g., screened for new shuffled sequences with improved properties, e.g., improved performance in detergents (see WO 97/07205).

Example 5

Shuffling of Lipolytic Enzyme Genes

PCR products of lipolytic enzyme genes are generated as in the previous example and pooled in equimolar amounts. The following mixture is generated in a suitable tube:

1 microliter PCR mixture (0.1 microgram), decamer random primer (300 pmol), 2 microliters 10* Klenow buffer (Promega), 0.25 mM dNTP, 2.5 mM $MgCl_2$ in a total volume of 20 microliters.

The mixture is set in a PE2400 thermocycler where the following program is run: 96° C. 5 minutes, 25° C. 5 minutes, 0.5 ml Klenow enzyme is added, 25° C. 60 minutes, 35° C. 90

This procedure generates a high number of small DNA polymers originating from all parts of the gene.

10 microliters is taken out for test on agarose gel.

10 microliters PCR mixture (0.25 mM dNTP, 1 microliter 10* Taq buffer (Perkin Elmer), 2.5 mM MgCl2, 0.5 microliter Taq enzyme) is added to the 10 microliters in the tube in the thermocycler. Then the following standard PCR-program is run: (94° C., 5 minutes) 1 cycle, (94° C. 30 seconds, 45° C., 30 seconds, 72° C. 30 seconds) 25 cycles, 72° C indefinite.

The PCR products are run on a 1.5% agarose gel. A clear unbiased smear is seen. DNA between 400 and 800 bp is isolated from the gel.

Half of the purified PCR product is mixed in a tube with two specific primers (40 pmol) flanking the gene of interest, 0.25 mM dNTP, 2 microliters 10* Taq buffer, 2.5 mM $MgCl_2$. Then the following standard PCR-program is run: (94° C., 5 minutes) 1 cycle, (94° C., 30 seconds, 50° C., 30 seconds, 72° C. 30 seconds) 25 cycles, 72° C. 7 minutes, 4° C. indefinite.

The PCR product is run on a 1.5% agarose gel. A band of the expected size is isolated. Additional PCR is run using specific primers (as mentioned above) in order to amplify the PCR-product before cloning.

The PCR-product and the desired vector are cut with the appropriate restriction enzymes (BamHI/XhoI). The vector and the PCR product are run on a 1.5% agarose gel, and purified from the gel.

The cut PCR-product and the cut vector are mixed in a ligase buffer with T4 DNA ligase (Promega). After overnight ligation at 16° C. the mixture is transformed into *E. coli* strain DH5a.

Example 6

Creation of Intron-Less Lipase Genes

A number of lipase genes with homology to the *Thermomyces lanuginosus* lipase gene were cloned. These genes were cloned as genomic DNA and were thus known to contain introns.

The intention was to shuffle these genes in order to obtain chimeric genes. In order to obtain the highest possible quality of library, the introns had to be removed. This was done by creating DNA oligos matching each flank of an exon as well as having a DNA sequence, which is homologous to the next neighbor exon.

These oligos were used in standard PCR (as known to a person skilled in the art), thus creating PCR fragments covering each and every exon (coding sequence) in the gene. These PCR fragments were purified from a 1% agarose gel. The PCR fragments were assembled into a full length gene, in a second PCR using the DNA oligos flanking the whole gene, as primers.

The PCR fragment containing the full length intron-less gene encoding the lipase was cloned into pENI 1960 as described in patent application PCT/DK02/00050.

The following primers were used to assemble each intron-less gene:

*Talaromyces thermophilus:* 051200j1, 051200J2, 051200J3, 051200J4, 051200J5, 051200J6, 051200J7 and 051200J8 (SEQ ID NO: 11-18), thus creating pENI2178, when cloned into pENI1960.

*Talaromyces emersonii:* 051200J9, 051200J10, 051200J11, 051200J12, 051200J13, 051200J14, 051200J15 and 051200J16 (SEQ ID NO: 19-26), thus creating pENI2159, when cloned into pENI1960.

*Thermomyces ibadanensis:* 051200J17, 051200J18, 051200J19, 051200J20, 051200J21, 051200J22, 051200J23 and 051200J24 (SEQ ID NO: 27-34), thus creating pENI2160, when cloned into pENI1960.

*Talaromyces byssochlamydoides:* 080201P1, 080201P2, 080201P3, 080201P4, 080201P5, 080201P6, 080201P7 and 080201P8 (SEQ ID NO: 54-61), thus creating pENI2230 when cloned into pENI1960.

Example 7

Shuffling of the Intron-Less Lipase Genes

A method using dUTP and uracil-DNA glycosylase was employed in order to make DNA fragments in sufficient quantities for DNA shuffling. The 3 genes *T. lanuginosus, T. thermophilus* and *T. ibadanensis* are quite homologous to each other (thus named Group A) as are *T. emersonii* and *T. byssochlamydoides* (named Group B). Thus in order to improve recombination between the two groups the following PCR scheme (see FIG. 1) was employed, using the following templates: pENI2178, pENI2159, pENI2160, pENI2230, and the *T. lanuginosus* gene cloned into pENI1902 (cut BamHI and SacII) (patent application PCT/DK02/00050).

The following oligonucleotides are shown in FIG. 1: 1298-taka, 19670, 19672, 115120 and 050401P6 (SEQ ID NOS: 62-65 and 68). 050401P1 (SEQ ID NO: 66) hybridizes to 5' *T lanuginose* lipase gene. 030501P1 (SEQ ID NO: 67) hybridizes to 5" of the other 4 lipase genes.

The final PCR fragment was cut first with BstEII and then with SfiI, as was the vector pENI2376. pENI2376 is a derivative of pENI1861(patent application PCT/DK02/00050)

The vector and PCR-fragment was purified from a 1% gel and ligated O/N. The ligated DNA pool was transformed into electro-competent *E. coli* DH10B, thus creating a library of app. 700.000 independent clones.

This library can be screened for activity towards various substrates such as Lecithin, DGDG, triglycerides such as tributyrine, olive oil, PNP-valerate or PNP-palmitate at different conditions such as high pH, low pH, high temperature, in presences of detergent, in the presence of ions or in the absence of ions.

This can be done in order to find, e.g., a thermo-stable lipase, a detergent phospholipase, a detergent lipase with first-wash performance, and no activity at neutral pH and so forth.

DNA-oligos:

1298-taka:
gcaagcgcgcgcaatacatggtgttttgatcat (SEQ ID NO:62)

19670:
ccccatcctttaactatagcg (SEQ ID NO:63)

19672:
ccacacttctcttccttcctc (SEQ ID NO:64)

115120:
gctttgtgcagggtaaatc (SEQ ID NO:65)

050401P1:
cggccgggccgcggaggccagggatccaccatgagg (SEQ ID NO:66)
agctcccttgtgctg

030501P1:
cggccgggccgcggaggccacaagtttgtacaaaaa (SEQ ID NO:67)
agcagg
(hybridizes to 5' of the other
4 lipase genes)

050401P6:
cggccgggtcaccccccatcctttaactatagcg (SEQ ID NO:68)

Example 8

Characterization of Lipolytic Enzymes

Lipolytic enzymes from *Thermomyces ibadanensis* and *Talaromyces thermophilus* were prepared as described above, purified and used for characterization.

The specific lipase activity was determined by the LU method described in WO 00/32758, and the amount of enzyme protein was determined from the optical density at 280 nm. The specific activity was found to be 3181 LU/mg for the *Th. ibadanensis* lipase and 1000 LU/mg for the *Tal. thermophilus* lipase.

The pH-activity relation was found by determining the lipase by the LU method at pH 5, 6, 7, 8, 9 and 10. Both enzymes were found to have the highest lipase activity at pH 10. The *Th. ibadanensis* lipase showed a broad optimum with more than 50% of maximum activity in the pH range 6-10 whereas the *Tal. thermophilus* lipase showed a stronger activity drop at lower pH with less than 30% of maximum activity at pH 5-8.

The thermostability was determined by differential scanning calorimetry (DSC) at pH 5 (50 mM acetate buffer), pH 7 (50 mM HEPES buffer) and pH 10 (50 mM glycine buffer) with a scan rate of 90° C./hr. The temperature at the top of the denaturation peak ($T_d$) was found to be as follows:

| | $T_d$ (° C.) | |
|---|---|---|
| pH | *T. ibadanesis* | *T. thermophilus* |
| 5 | 74* | 72* |
| 7 | 72 | 75 |
| 10 | 64 | 69 |

Example 9

Lysophospholipase Activity

Purified lipolytic enzymes from *T. ibadanensis* and *T. thermos* were tested by incubating with lysolecithin as substrate at pH 5 and 7, and the extent of reaction was followed by use of NEFA kit.

The results were that the enzyme from *T. ibadanensis* showed high lysophospholipase activity at pH 5 and some activity at pH 7. The enzyme from *T. thermos* showed a slight activity.

The invention claimed is:

1. An isolated polypeptide which has lipolytic enzyme activity and which has an amino acid sequence which has at least 95% sequence identity with the mature polypeptide of SEQ ID No: 6.

2. The polypeptide of claim 1, which has an amino acid sequence which is the mature peptide of SEQ ID NO: 6.

3. The polypeptide of claim 1, which is native to a strain of *Thermomyces ibadanensis*.

4. The polypeptide of claim 1, which is encoded by a DNA sequence cloned into a plasmid present in *Escherichia coli* deposit number DSM 14049.

5. A detergent composition composing a polypeptide of claim 1 and a surfactant.

6. A flour composition comprising a flour and a polypeptide of claim 1.

7. A process for producing a dough or a baked product made from a dough, comprising adding to the dough a polypeptide of claim 1.

* * * * *